US010252251B2

(12) United States Patent
Lin et al.

(10) Patent No.: US 10,252,251 B2
(45) Date of Patent: Apr. 9, 2019

(54) PRODUCTION OF ORGANIC MATERIALS USING SOLID CATALYSTS

(71) Applicant: Board of Regents of the Nevada System of Higher Education, on Behalf of the University of Nevada, Reno, Reno, NV (US)

(72) Inventors: Hongfei Lin, Pullman, WA (US); Lisha Yang, Reno, NV (US)

(73) Assignee: Board of Regents of the Nevada System of Higher Education, on Behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 15/249,166

(22) Filed: Aug. 26, 2016

(65) Prior Publication Data

US 2017/0057903 A1 Mar. 2, 2017

Related U.S. Application Data

(60) Provisional application No. 62/211,585, filed on Aug. 28, 2015.

(51) Int. Cl.
*B01J 29/03* (2006.01)
*B01J 29/70* (2006.01)
*B01J 35/00* (2006.01)
*B01J 35/10* (2006.01)
*C07C 67/00* (2006.01)
*C07C 69/68* (2006.01)

(52) U.S. Cl.
CPC ....... *B01J 29/7049* (2013.01); *B01J 29/0308* (2013.01); *B01J 35/002* (2013.01); *B01J 35/1023* (2013.01); *B01J 35/1042* (2013.01); *B01J 35/1047* (2013.01); *B01J 35/1061* (2013.01); *C07C 67/00* (2013.01)

(58) Field of Classification Search
CPC ................ B01J 35/1047; B01J 35/1061; B01J 35/1042; B01J 35/1023; B01J 35/002; B01J 29/7049; B01J 29/0308; C07C 67/00
See application file for complete search history.

(56) References Cited

U.S. PATENT DOCUMENTS 8,778,401 B2 7/2014 Shen et al.
2005/0133052 A1 6/2005 Fournier et al.
(Continued)

FOREIGN PATENT DOCUMENTS

WO WO 2015024875 * 2/2015

OTHER PUBLICATIONS

Melero ("Zr-SBA-15 acid catalyst: Optimization of the synthesis and reaction conditions for biodiesel production from low-grade oils and fats" Catalysis Today, 195, 2012, p. 44-53).*
(Continued)

Primary Examiner — Amy C Bonaparte
(74) Attorney, Agent, or Firm — Klarquist Sparkman, LLP

(57) ABSTRACT

The present disclosure provides a method for producing organic compounds, such as esters, from an organic feedstock that includes at least one of a biopolymer or a lipid. The method includes heating the feedstock in the presence of a solid catalyst, such as a solid, inorganic Lewis acid catalyst, and reaction medium that includes an alcohol. At least certain ester products have an ester group corresponding to a substituent of the alcohol.

20 Claims, 26 Drawing Sheets

(56) References Cited

U.S. PATENT DOCUMENTS

| | | | | |
|---|---|---|---|---|
| 2010/0121096 A1* | 5/2010 | Taarning | ............... | C07C 51/00 560/179 |
| 2013/0079566 A1* | 3/2013 | Lin | ..................... | C07C 51/21 585/242 |

OTHER PUBLICATIONS

Iglesias ("Zr-SBA-15 as an efficient acid catalyst for FAME production from crude palm oil" Cat Today 167, 2011, p. 46-55).*

Gracia ("Evidences of the in situ generation of highly active Lewis Acid species on Zr-SBA-15" Applied Cat A: general, 371, 2009, p. 85-91).*

Melero 2005 ("Direct synthesis of titanium-substituted mesostructured materials using non-ionic surfactants and titanocene dichloride" Microporous and Mesoporous Materials, 86, 2005, p. 364-373).*

Liu ("Synthesis of Zr-grafted SBA-15 as an efffective support for cobalt catalyst in Fischer-Tropsch Synthesis" Chemistry letters, 37, 9, 2008, p. 984-985).*

Ojeda ("On comparing BJH and NLDFT pore size distributions determined from N2 soprtionon SBA-15 substrata" Phys Chem 2003, 5, p. 1859-1866).*

Marshall ("Liquid-Vapor Critical Temperatures of Several Aqueous-Organic and Organic-Organic solution Systems" J. inorg. Nucl. Chem. 1974, vol. 36, p. 2319-2323).*

Kuwahara ("Esterification of levulinic acid with ethanol over sulfated mesoporous zirconosilicates: Influences of the preparation conditions on the structural properties and catalytic performances" Catalysis Today 237, 2014, p. 18-28).*

Thitsartarn ("Transesterification of Oil by Sulfated Zr-Supported Mesoporous Silica" Ind. Eng. Chem. Res. 2011, 50, p. 7857-7865).*

Mariani ("Some insight into the role of different copper species as acids in cellulose deconstruction" Catalysis Communications, vol. 44, 2014, p. 19-23) (Year: 2014).*

Li ("Preparation of Sulfo-Group-Bearing Mesoporous-Silica-Based Solid Acid Catalyst and Its Application to Direct Saccharification" Journal of Chemical Engineering of Japan, vol. 45, No. 7, p. 484-492, 2012) (Year: 2012).*

"(129d) Catalytic Conversion of Xylan to Value-Added Carboxylic Acids," retrieved from https://www.aiche.org/conferences/aicheannualmeeting/2012/proceeding/paper/129dcatalyticconversionxylanvalueaddedcarboxylicacids, or before Oct. 16, 2017, 3 pages, Abstract on.

"Abstract: Catalytic Conversion of Hemicellulosic Biomass to Lactic Acid in Aqueous Phase Media (2013 Annual Meeting)," retrieved from https://aiche.confex.com/aiche/2013/webprogram/Paper332917.html, on or before Oct. 16, 2017, 1 page.

"Synthesis and Structural Studies of MCM-41 and SBA-15 Type Mesoporous Silicates," Ph.D. Theses, Solymar Edit, University of Szeged, Department of Applied and Environmental Chemistry, 11 pages, 2005.

Alonso et al. "Direct conversion of cellulose to levulinic acid and gamma-valerolactone using solid acid catalysts," *Catalysis Science & Technology*, 3(4): 927-931, 2012.

Holm et al., "Sn-Beta catalysed conversion of hemicellulosic sugars," *Green Chemistry*, 14: 702-706—2012.

Sayari and Jaroniec, "SBA-15 versus MCM-41: are they the same materials?" *Studies in Surface Science and Catalysis*, 141: 395-402, 2002.

Vallet-Regi et al., "Mesoporous Materials for Drug Delivery," *Angew. Chem. Int. Ed.*, 46: 7548-7558, 2007.

Weingarten et al., "Design of solid acid catalysts for aqueous-phase dehydration of carbohydrates: The role of Lewis and Bronsted acid sites," *Journal of Catalysis*, 279, 174-182, 2011.

Yang et al., "(338g) Direct Conversion of Cellulosic Biomass to Alkyl Lactates on Mesoporous Zr-Silicates," retrieved from https://www.aiche.org/conferences/aicheannualmeeting/2015/proceeding/paper/338gdirectconversioncellulosicbiomassalkyllacatateonmesoporouszrs, on or before Oct. 16, 2017, 3 pages, Abstract.

Yang et al., "Catalytic Conversion of Hemicellulosic Biomass to Lactic Acid in Aqueous Phase Media," *AIChE Annual Meeting*, San Francisco, CA, 2013, Nov 3-8, 20 pages (Nov. 7, 2013).

Yang et al., "Catalytic conversion of hemicellulosic biomass to lactic acid in pH neutral aqueous phase media," *Applied Catalysis B: Environmental*, 162: 149-157, 2015.

Yang et al., "Direct Conversion of Cellulose into Ethyl Lactate in Supercritical Ethanol-Water Solutions," *ChemSusChem*, 9: 36-41, 2016.

Yang et al., "Direct Conversion of Cellulosic Biomass to Alkyl Lactates on Mesoporous Zr-Silicates," 2015 AIChE Annual Meeting, 25 pages, Nov. 10, 2015.

Yang et al., "Effect of redox properties of LaCoO$_3$ perovskite catalyst on production of lactic acid from cellulosic biomass," *Catalysis Today*, 269: 56-64, 2016.

Yang et al., "Mechanistic insights into the production of methyl lactate by catalytic conversion of carbohydrates on mesoporous Zr-SBA-15," *Journal of Catalysis*, 207-216, 2016.

Yang et al., Catalytic Conversion of Lignocellulosic Biomass to Carboxylic Acids and Derivatives, University of Nevada, Reno, 203 pages, 2015.

\* cited by examiner

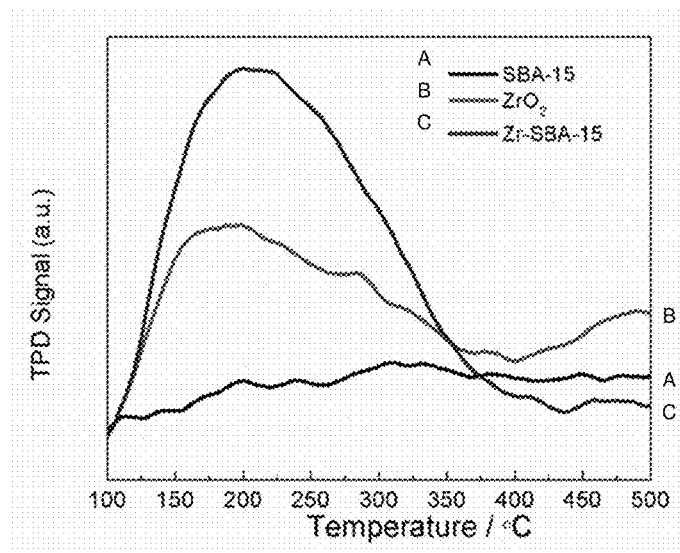

FIG. 2

| Catalyst | BET Surface area[a] / m²g⁻¹ | Pore volume determined by NLDFT model[b] / cm³g⁻¹ | Pore size determined by NLDFT model[b] / nm | Acid strength NH₃ Quantity (mmol/g) |
|---|---|---|---|---|
| SBA-15 | 876 | 0.998 | 7.0 | 0.02 |
| Zr-SBA-15 | 841 | 1.357 | 9.1 | 0.72 |

[a]BET surface area calculated using the BET (Bruanauer-Emmett-Teller) equation at relative pressures between 0.05 and 0.25 using the adsorption branch.

[b]Cylindrical pore model applied for $N_2$ adsorption on silica at 77K for the adsorption branch.

FIG. 3

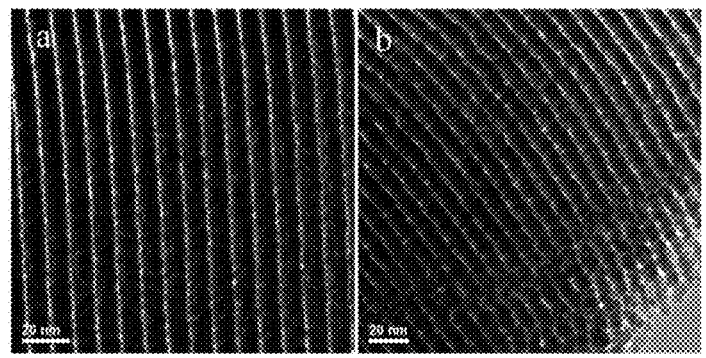

FIG. 6

| Entry | Catalyst | Solvent | Carbon Yield/% | | | | | | S.R./% |
|---|---|---|---|---|---|---|---|---|---|
| | | | EL | ADA | C4 | ELE | Furfural | HMF | |
| 1 | / | 95% ethanol | 2.1 | 8.7 | 1.0 | 0.2 | 0.8 | 6.6 | 52.3 |
| 2 | SBA-15 | 95% ethanol | 5.1 | 6.0 | 1.8 | 0.3 | 2.2 | 5.7 | 19.5 |
| 3 | $ZrO_2$ | 95% ethanol | 8.2 | 12.3 | 2.3 | 0.6 | 0.1 | 0.1 | 34.5 |
| 4 | Zr-SBA-15 | 95% ethanol | 30.1 | 26.7 | 13.5 | 2.2 | 0.3 | 0.1 | 8.6 |
| 5[a] | Zr-SBA-15 | 95% ethanol | 26.7 | 21.3 | 10.6 | 1.2 | 0.2 | 0.1 | 16.1 |
| 6[b] | Zr-SBA-15 | 95% ethanol | 24.9 | 15.3 | 6.3 | 0.6 | 0.4 | 0.1 | 33.8 |
| 7 | Zr-SBA-15 | Water | 1.4[c] | / | / | 20.9[d] | 0.7 | 14.6 | / |

Reaction condition: 260 °C, 400 psi initial pressure of $N_2$, 20g solvent (95% ethanol and 5% water), 6 hours, 0.2g cellulose, 0.1g catalyst. EL: Ethyl lactate; ADA: Acetaldehyde diethyl acetal; C4: Ethyl 2-hydroxybutanoate; ELE: Ethyl levulinate. [a] 1g cellulose, 0.5g catalyst, [b] 2g cellulose, 1g catalyst, [c] lactic acid, [d] levulinic acid.

FIG. 7

| Ethanol | | Water | | Supercritical Pressure psi | Supercritical Temperature °C |
| --- | --- | --- | --- | --- | --- |
| Mole percentage% | Weight percentage% | Mole percentage% | Weight percentage% | | |
| 100 | 100 | 0 | 0 | 922 | 242 |
| 95 | 98.0 | 5 | 2.0 | 950 | 243 |
| 90 | 95.8 | 10 | 4.2 | 975 | 245 |
| 85 | 93.5 | 15 | 6.5 | 1000 | 247 |
| 80 | 91.1 | 20 | 8.9 | 1060 | 250 |
| 75 | 88.5 | 25 | 11.5 | 1090 | 253 |
| 70 | 85.6 | 30 | 14.4 | 1120 | 256 |
| 65 | 82.6 | 35 | 17.4 | 1190 | 259 |
| 60 | 79.3 | 40 | 20.7 | 1250 | 263 |
| 55 | 75.8 | 45 | 24.3 | 1300 | 268 |
| 50 | 71.9 | 50 | 28.1 | 1370 | 274 |

Comparison of the conversion of different carbohydrate feedstocks with the Zr-SBA-15 catalyst in methanol and/or water solvents.

| Entry | Feedstock | Catalyst | Time/h | Solvent | Carbon Yield/% | | | | | |
|---|---|---|---|---|---|---|---|---|---|---|
| | | | | | ML | GADMA | MG | MLE | Furfural | HMF |
| 1 | Xylose | / | 1h | Methanol | 8.1 | 7.9 | 6.3 | / | / | / |
| 2 | Xylose | Zr-SBA-15 | 1h | Methanol | 35.9 | 1.6 | 0.2 | / | / | / |
| 3 | Xylose | / | 1h | Water | 3.0(Lactic acid) | / | / | / | 21.2 | / |
| 4 | Xylose | Zr-SBA-15 | 1h | Water | 5.9(Lactic acid) | / | / | / | 42.3 | / |
| 4 | Glyceraldehyde | / | 1h | Methanol | 19.9 | 2.3 | 2.9 | / | / | / |
| 5 | Glyceraldehyde | Zr-SBA-15 | 1h | Methanol | 78.8 | 2.5 | 0.8 | / | / | / |
| 6 | Dihydroxy acetone | / | 1h | Methanol | 29.5 | 1.9 | 3.3 | / | / | / |
| 7 | Dihydroxy acetone | Zr-SBA-15 | 1h | Methanol | 84.5 | 1.9 | 0.9 | / | / | / |
| 8 | Pyruvaldehyde | / | 1h | Methanol | 64.5 | 0.7 | 0.2 | / | / | / |
| 9 | Pyruvaldehyde | Zr-SBA-15 | 1h | Methanol | 98.7 | 0.8 | 0.2 | / | / | / |
| 10 | Glycoaldehyde | / | 1h | Methanol | 3.9 | 32.6 | 0.7 | / | / | / |
| 11 | Glycoaldehyde | Zr-SBA-15 | 1h | Methanol | 61.3 | 8.4 | 0.6 | / | / | / |
| 12 | GADMA | Zr-SBA-15 | 1h | Methanol | 24.0 | / | 0.2 | / | / | / |
| 13 | Xylose | Zr-SBA-15 | 6h | Methanol | 40.8 | 0.6 | 0.5 | 2.7 | 3.2 | / |
| 14 | Glucose | Zr-SBA-15 | 6h | Methanol | 37.3 | 0.6 | 1.0 | 1.3 | 0.9 | 0.2 |
| 15 | Sucrose | Zr-SBA-15 | 6h | Methanol | 39.5 | 0.4 | 0.3 | 2.5 | 1.6 | 2.2 |
| 16 | Fructose | Zr-SBA-15 | 6h | Methanol | 44.1 | 0.7 | 0.6 | 3.1 | 1.7 | 1.7 |
| 17 | Galactose | Zr-SBA-15 | 6h | Methanol | 14.8 | 0.8 | 0.1 | 7.2 | 0.9 | 2.1 |
| 18 | Mannose | Zr-SBA-15 | 6h | Methanol | 31.3 | 1.2 | 0.3 | 8.9 | 1.3 | 1.6 |
| 19 | Arabinose | Zr-SBA-15 | 6h | Methanol | 33.4 | 1.3 | 0.5 | 5.4 | 3.7 | 0.1 |
| 20 | Cellobiose | Zr-SBA-15 | 10h | Methanol | 24.3 | 0.9 | 0.3 | 4.8 | 1.9 | 2.1 |
| 21 | Cellobiose | Zr-SBA-15 | 10h | 95% Methanol | 26.4 | 1.6 | 0.1 | 3.1 | 2.3 | 1.3 |
| 22 | Cellulose | Zr-SBA-15 | 10h | Methanol | 16.7 | 0.1 | 0.1 | 0.7 | 0.2 | 0.7 |
| 23 | Cellulose | Zr-SBA-15 | 10h | 95% Methanol | 28.1 | 0.3 | 0.4 | 2.0 | 1.8 | 1.0 |
| 24 | Starch | Zr-SBA-15 | 10h | Methanol | 24.1 | 1.4 | 0.1 | 0.9 | 0.1 | 0.2 |
| 25 | Starch | Zr-SBA-15 | 10h | 95% Methanol | 26.8 | 0.7 | 0.2 | 1.1 | 0.6 | 1.5 |

Reaction conditions: 240 °C, 400 psi initial $N_2$ pressure, 0.2 g biomass substrate, and 0.1 g Zr-SBA-15. ML: Methyl lactate, GADMA: Glycolaldehyde dimethyl acetal, MG: Methyl glycolate, MLE: Methly levulinate.

FIG. 27

Comparison of the effect of different pore sizes of Zr-SBA-15 on the catalytic conversion of xylose to methyl lactate in methanol solvent.

| Entry | Feedstock | Catalyst | Conversion | Solid residue | Carbon Yield/% | | | | |
|---|---|---|---|---|---|---|---|---|---|
| | | | | | ML | GDA | MG | MLE | Furfural |
| 1 | Xylose | Zr-SBA-15-80°C | >99% | 17.4% | 30.9 | 1.0 | 0.1 | 0.6 | 9.2 |
| 2 | Xylose | Zr-SBA-15-100°C | >99% | 10.8% | 35.9 | 1.6 | 0.2 | 0.3 | 7.9 |
| 3 | Xylose | Zr-SBA-15-120°C | >99% | 9.2% | 34.1 | 3.0 | 1.0 | 0.2 | 7.3 |
| 4 | Xylose | Zr-SBA-15-150°C | >99% | 6.9% | 34.3 | 8.7 | 1.2 | 0.2 | 6.4 |

Reaction conditions: 240 °C, 1h, 400 psi $N_2$ pressure, 0.2g feedstock loading, and 0.1 g catalyst. ML: Methyl lactate, GADMA: Glycolaldehyde dimethylacetal, MG: Methyl glycolate, MLE: Methly levulinate.

FIG. 29

Physicochemical properties of Zr-SBA-15 silicates.

| Catalyst[a] | BET Surface area[b] / m²g⁻¹ | Pore volume determined by NLDFT model[c] / cm³g⁻¹ | Pore size determined by NLDFT model[c] / nm | Acid strength NH₃ Quantity (mmol/g) |
|---|---|---|---|---|
| SBA-15-100°C | 876 | 0.998 | 7.0 | 0.02 |
| Zr-SBA-15-80°C | 988 | 1.275 | 7.6 | 0.65 |
| Zr-SBA-15-100°C | 841 | 1.357 | 9.1 | 0.72 |
| Zr-SBA-15-120°C | 618 | 1.384 | 9.8 | 0.69 |
| Zr-SBA-15-150°C | 393 | 1.215 | 10.6 | 0.51 |

[a] The mole ratio of Si/Zr is 20 for the catalysts.
[b] BET surface area calculated using the BET (Brunauer-Emmett-Teller) equation at relative pressures between 0.05 and 0.25 using the adsorption branch.
[c] Cylindrical pore model applied for N₂ adsorption on silica at 77K for the adsorption branch.

FIG. 30

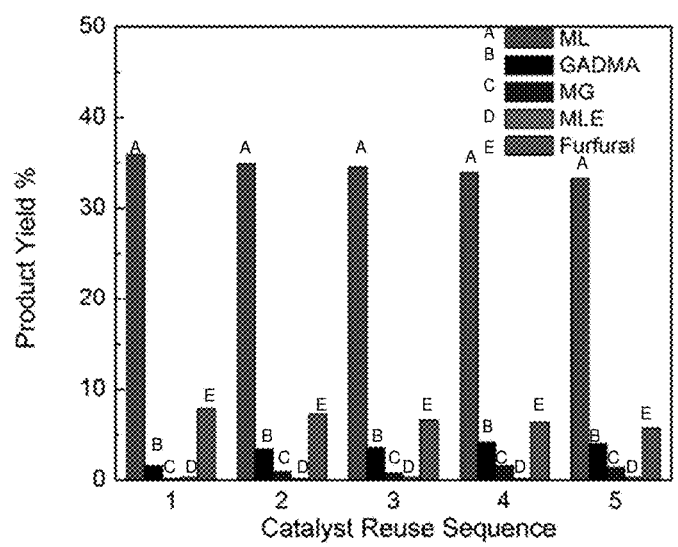

FIG. 31

PRODUCTION OF ORGANIC MATERIALS USING SOLID CATALYSTS

CROSS REFERENCE TO RELATED APPLICATION

This application claims the benefit of, and incorporates by reference, U.S. Provisional Patent Application Ser. No. 62/211,585, filed Aug. 28, 2015.

STATEMENT OF GOVERNMENT SUPPORT

This invention was made with government support under Grant No. CBET 1337017 awarded by the National Science Foundation. The government has certain rights in the invention.

FIELD

This disclosure relates generally to the production of organic materials from an organic feedstock that includes a biopolymer, a lipid, or mixtures thereof, using a solid catalyst. In particular embodiments, esters are produced from a biopolymer-containing feedstock using a solid, inorganic catalyst having a combination of Lewis acid and Brønsted acid sites.

SUMMARY

Disclosed herein are embodiments of a method for producing organic compounds from an organic feedstock containing a biopolymer or lipid by heating the feedstock in the presence of a solid catalyst and an alcohol. In certain implementations, the feedstock includes a biopolymer. In a particular example, the feedstock includes a polysaccharide, such as cellulose or cellobiose, lignin, or a polypeptide. In further examples, the feedstock includes biomass, such as cellulosic, lignocellulosic, or algal biomass.

In particular implementations, the catalyst has a mixture of Brønsted acid sites and Lewis acid sites, such as at a ratio of between about 1:100 and 100:1, between about 1:10 and 10:1, or between about 1:20 and about 3:20. The acidity of the catalyst, as measured by temperature-programmed desorption of ammonia, can be selected to be between about 0.2 mmol/g $NH_3$ and about 10 mmol/g $NH_3$, such as between about 0.1 mmol/g $NH_3$ and about 5 mmol/g $NH_3$ or between about 0.2 mmol/g $NH_3$ and about 1 mmol/g $NH_3$.

In further implementations, the catalysts are porous and selected to have a mean pore diameter of between about 2 nm and about 50 nm, such as between about 2 nm and about 20 nm, and a mean pore volume of between about 0.2 $cm^3/g$ and about 15 $cm^3/g$, such as between about 0.8 $cm^3/g$ and about 1.75 $cm^3/g$, and a surface area of between about 100 $m^2/g$ and about 5000 $m^2/g$, such as between about 300 $m^2/g$ and about 2000 $m^2/g$.

In some aspects, the catalyst can be used with a co-catalyst, or a substance used to modify the properties of the catalyst. In particular examples, the catalyst is modified with one or more alkali metal halides, such as by adding an alkali metal halide to the reaction mixture, or contacting the catalyst with an alkali metal halide before adding the catalyst to the reaction mixture. In a specific example, the alkali metal halide is potassium chloride. The alkali metal halide can be added in an amount relative to the amount of catalyst, such as adding between about 0.001 wt % and about 5 wt % alkali metal halide, such as between about 0.001 wt % and about 0.5 wt %.

The reaction is typically carried out at a temperature, and for a time period, sufficient to achieve a desired yield or distribution of products. In certain implementations, the reaction is carried out for between about 30 seconds and about 24 hours, such as between about 15 minutes and about 12 hours or between about 30 minutes and about 10 hours, at a temperature of between about 180° C. and about 400° C., such as between about 200° C. and about 360° C. or between about 220° C. and about 300° C. In particular examples, the reaction temperature is about the supercritical temperature, such as at least about 75% of the supercritical temperature, for a medium in which the reaction occurs, such as an alcohol or an alcohol-water mixture. In further examples, the reaction is carried out under subcritical conditions or under supercritical conditions.

The reaction is carried out in the presence of an alcohol, for example, one or more C1-C15 alcohols, such as alkyl alcohols, including methanol or ethanol. In some examples, the alcohol is present as an alcohol-water mixture, such as a mixture containing between about 0.1 wt % water and about 90 wt % water, such as between about 0.5 wt % water and about 25 wt % water or between about 1 wt % water and about 15 wt % water.

There are additional features and advantages of the various embodiments of the present disclosure. They will become evident from the following disclosure.

In this regard, it is to be understood that this is a summary of the various embodiments described herein. Any given embodiment of the present disclosure need not provide all features noted above, nor must it solve all problems or address all issues any prior art noted herein.

BRIEF DESCRIPTION OF THE DRAWINGS

Various embodiments are shown and described in connection with the following drawings in which:

FIG. 2 is a graph of temperature programmed desorption signal versus temperature (° C.) illustrating the temperature-programmed desorption of ammonia ($NH_3$-TPD) for $ZrO_2$, pure SBA-15, and Zr-SBA-15 materials.

FIG. 3 is a table illustrating physical and chemical properties of pure SBA-15 and Zr-SBA-15.

FIG. 6 is high-resolution transmission electron microscopy (HRTEM) images of (a) fresh Zr-SBA-15; and (b) Zr-SBA-15 after being used three times and then calcined in flowing air at 550° C. for 6 hours.

FIG. 7 is a table comparing yields of the main products of cellulose conversion with and without catalysts ($ZrO_2$ or Zr-SBA-15) for reactions carried out in various solvents.

FIG. 27 is a table comparing the conversion of different carbohydrate feedstocks with Zr-SBA-15 catalyst in methanol and/or water solvents for various reaction times.

FIG. 29 is a table comparing the effect of different pore sizes of Zr-SBA-15 on the catalytic conversion of xylose to methyl lactate in methanol solvent.

FIG. 30 is a table listing the physicochemical properties of Zr-SBA-15 silicates.

FIG. 31 is a graph of product yield (%) versus number of reactions for which un-regenerated Zr-SBA-15 catalyst was reused in the conversion of 0.2 g xylose at 240° C. for 1 hour at an initial $N_2$ pressure of 400 psi using 0.1 g catalyst.

DETAILED DESCRIPTION

Unless otherwise explained, all technical and scientific terms used herein have the same meaning as commonly understood by one of ordinary skill in the art to which this disclosure pertains. The singular terms "a," "an," and "the" include plural referents unless the context clearly indicates otherwise. Similarly, the word "or" is intended to include "and" unless the context clearly indicates otherwise. The term "includes" means "comprises." The terms "solvent," "a solvent," and "the solvent" include one or more than one individual solvent unless indicated otherwise. Mixing solvents that include more than one individual solvent with other materials can include mixing the individual solvents simultaneously or serially unless indicated otherwise. Any separations and extractions described herein can be partial, substantial, or complete separations unless indicated otherwise. All percentages recited herein are weight percentages unless indicated otherwise. All numerical ranges given herein include all values, including end values (unless specifically excluded) and intermediate ranges.

Figure 1:
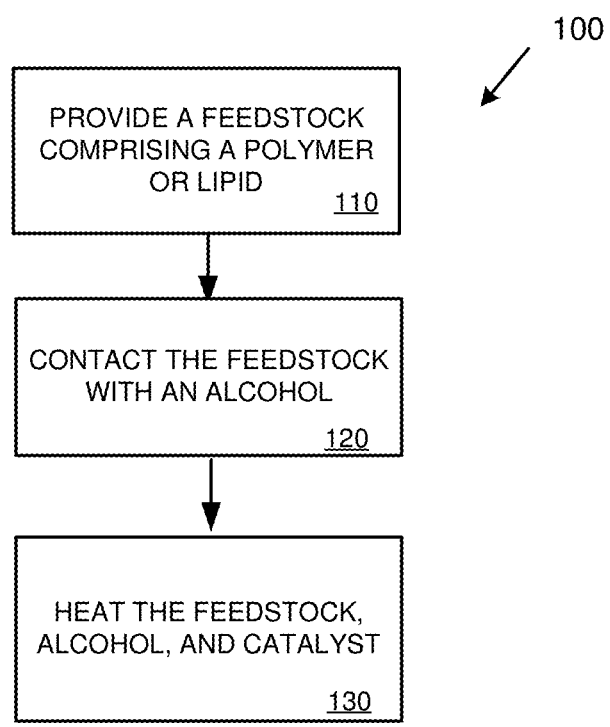
FIG. 1 is a flowchart illustrating a method of forming organic compounds from a feedstock that includes a biopolymer or a lipid using a solid, inorganic catalyst according to an embodiment of the present disclosure.

FIG. 1 provides a flowchart of a method 100 representing a general embodiment of the present disclosure for producing organic materials using a solid catalyst, such as a solid inorganic catalyst. In step 110, a feedstock that includes a biopolymer or a lipid is provided. In step 120, the feedstock is contacted with an alcohol, such as an alcohol for which the corresponding ester is desired. For example, if methyl esters are desired, the alcohol may be methanol. If ethyl esters are desired, the alcohol may be ethanol. In step 130, the feedstock and alcohol are heated in the presence of a suitable catalyst to form organic products, such as esters.

In a particular implementation, the biopolymer feedstock includes a polymeric carbohydrate. Suitable carbohydrate feedstocks can include oligosaccharides, polysaccharides, or mixtures thereof. In particular examples, the carbohydrate feedstock includes one or more glucans, such as cellulose, chrysolaminarin, starch, callose, dextran, glycogen, pullulan, curdian, laminarin, lentinan, lichenin, pleuran, or zymosan. In other examples, the carbohydrate feedstock includes hemicelluloses, such as xylan, glucuronoxylan, arabinoxylan, glucomannan, and xyloglucan. Further examples of suitable carbohydrates include cellobiose, chitin, pectin, mannan, fuciodan, galactomannan, amylose, amylopectin, and glycogen.

In a further implementation, the feedstock includes polypeptides, proteins, lignins, or mixtures thereof.

The feedstock, in another implementation, includes lipids.

The feedstock can include mixtures of the above-described biopolymers or the above-described biopolymers and lipids. In some implementations, the feedstock is provided as an isolated material. In other implementations, the organic feedstock is present with other materials, such as other organic materials, which may (but not necessarily) be reactive with the solid catalyst to produce an organic product.

For example, the feedstock may include biomass, such as a cellulosic, lignocellulosic, or algal biomass, with the organic feedstock being supplied by various constituents of the biomass. In some implementations, the biomass is supplied as raw, untreated biomass. In other implementations, the biomass may be subjected to one or more pretreatment steps, such as dewatering, drying, sugar extraction, lipid extraction, or steps to remove or breakdown certain biomass constituents, such as proteins or lignin. Particular types of biomass that may be used as feedstocks include agricultural waste, such as corn stover, sugarcane bagasse, and manure.

In certain implementations, the solid catalyst is an inorganic catalyst, such as inorganic catalysts having Lewis acid properties. In various examples, the Lewis acid catalyst is selected from metal oxides of Zr, Ti, Sn, Nb, and Cs. In further examples, the Lewis acid catalyst has ions of Zr, Ti, Sn, Nb, Ga, or Ge incorporated into a zeolite material. In a specific example, the zeolite material is Sn-beta.

In yet further examples, the catalyst is a mesoporous material that has metal ions incorporated into the catalyst framework, such as being isomorphically substituted with metal ions. In particular examples, the catalyst includes a mesoporous silica material, such as MCM-41, MCM-48, SBA-15, MCF, KIT-6, TUD-1, MSU, or CMK-3. Suitable metal ions for incorporation into the mesoporous material include transition metals, such as Zr, Ti, Sn, Nb, Ga, Ge, V, or Fe. The degree of doping, or substitution, can be varied to achieve desired catalyst properties. In various examples, the degree of doping results in a ratio of the native element in the mesoporous material, such as silicon, to transition metal, such as Zr, of between about 5:1 (silicon-to-dopant) and about 200:1, such as between about 10:1 and about 100:1, between about 20:1 and about 80:1, or between about 20:1 and about 40:1, including between 5:1 and 200:1, between 10:1 and 100:1, between 20:1 and 80:1, or between 20:1 and 40:1, such as 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 120:1, 125:1, 130:1, 135:1, 140:1, 145:1, 150:1, 155:1, 160:1, 165:1, 170:1, 175:1, 180:1, 185:1, 190:1, 195:1, or 200:1. In further examples, the ratio is at least about 5:1, such as at least about 10:1, or at least about 20:1, such as at least 5:1, at least 10:1, at least 20:1, including 5:1, 6:1, 7:1, 8:1, 9:1, 10:1, 11:1, 12:1, 13:1, 14:1, 15:1, 16:1, 17:1, 18:1, 19:1, or 20:1. In more particular examples, ratios listed as being "at least" a particular ratio refer to ratios having increasing amounts of dopant compared with the listed value, including values between, and including, the listed ratio and 5:1. Certain implementations result in the substituted transition metals being incorporated into a charge-neutral framework.

Certain disclosed catalysts may be characterized by their acid strength. One way of measuring acid strength is by temperature-programmed desorption of ammonia. In certain examples, the catalyst has an acidity, as measured by temperature-programmed desorption of ammonia, of between about 0.02 mmol/g $NH_3$ and about 10 mmol/g $NH_3$, such as between about 0.1 mmol/g $NH_3$ and about 5 mmol/g $NH_3$, between about 0.1 mmol/g $NH_3$ and about 2 mmol/g $NH_3$, between about 0.2 mmol/g $NH_3$ and about 1 mmol/g $NH_3$, between about 0.2 mmol/g $NH_3$ and about 0.8 mmol/g $NH_3$, between about 0.23 mmol/g $NH_3$ and about 0.76 mmol/g $NH_3$, between about 0.6 mmol/g $NH_3$ and about 0.8 mmol/g $NH_3$, or between about 0.7 mmol/g $NH_3$ and about 0.8 mmol/g $NH_3$, including between 0.02 mmol/g $NH_3$ and 10 mmol/g $NH_3$, between 0.1 mmol/g $NH_3$ and 5 mmol/g $NH_3$, between 0.1 mmol/g $NH_3$ and 2 mmol/g $NH_3$, between 0.2 mmol/g $NH_3$ and 1 mmol/g $NH_3$, between 0.2 mmol/g $NH_3$ and 0.8 mmol/g $NH_3$, between 0.23 mmol/g $NH_3$ and 0.76 mmol/g $NH_3$, between 0.6 mmol/g $NH_3$ and 0.8 mmol/g $NH_3$, or between 0.7 mmol/g $NH_3$ and 0.8 mmol/g $NH_3$, such as 0.02 mmol/g $NH_3$, 0.05 mmol/g $NH_3$, 0.075 mmol/g $NH_3$, 0.1 mmol/g $NH_3$, 0.25 mmol/g $NH_3$, 0.5 mmol/g $NH_3$, 0.75 mmol/g $NH_3$, 0.76 mmol/g $NH_3$, 0.8 mmol/g $NH_3$, 1 mmol/g $NH_3$, 1.5 mmol/g $NH_3$, 2 mmol/g $NH_3$, 2.5 mmol/g $NH_3$, 3 mmol/g $NH_3$, 3.5 mmol/g $NH_3$, 4 mmol/g $NH_3$, 4.5 mmol/g $NH_3$, 5 mmol/g $NH_3$, 5.5 mmol/g $NH_3$, 6 mmol/g $NH_3$, 6.5 mmol/g $NH_3$, 7 mmol/g $NH_3$, 7.5 mmol/g $NH_3$, 8 mmol/g $NH_3$, 8.5 mmol/g $NH_3$, 9 mmol/g $NH_3$, 9.5 mmol/g $NH_3$, or 10 mmol/g $NH_3$. In further examples, the catalyst has an acidity, as measured by temperature-programmed desorption of ammonia, greater than about 0.2 mmol/g $NH_3$, such as greater than about 0.25 mmol/g $NH_3$, greater than about 0.5 mmol/g $NH_3$, or greater than about 0.7 mmol/g $NH_3$, including greater than 0.2 mmol/g $NH_3$, such as greater than 0.25 mmol/g $NH_3$, greater than 0.5 mmol/g $NH_3$, or greater than 0.7 mmol/g $NH_3$. In more particular examples, listed acidities having "greater than" a particular acidity include values between, and including, the listed acidity value and 10.

As described above, in some aspects of the present disclosure, suitable catalysts have a mixture of Lewis acid sites and Brønsted acid sites. In some implementations, the catalysts have a Brønsted acid site-to-Lewis acid site ratio of between about 1:100 and about 100:1, such as between about 1:10 and about 10:1, between about 1:5 and about 4:5, between about 3:10 and about 7:10, between about 1:100 and about 2:1, between about 1:100 and about 1:1, between about 1:100 and about 1:2, between about 1:100 and about 1:5, between about 1:20 and about 1:5, or between about 1:20 and about 3:20, including between 1:100 and 100:1, such as between 1:10 and 10:1, between 1:5 and 4:5, between 3:10 and 7:10, between 1:100 and 2:1, between 1:100 and 1:1, between 1:100 and 1:2, between 1:100 and 1:5, between 1:20 and 1:5, or between 1:20 and 3:20, such as 1:100, 1:20; 1:10; 3:20, 1:5, 3:10, 1:2; 1:1, 2:1, 7:10, 4:5, 10:1, or 100:1. In further implementations, the catalysts have Lewis acids sites that are at least about 10% of the combined number of Lewis acid and Brønsted acid sites, such as at least about 15%, at least about 25%, at least about 50%, at least about 75%, at least about 85%, at least about 90%, or at least about 95%, including at least 10%, at least 15%, at least 25%, at least 50%, at least 75%, at least 85%, at least 90%, or at least 95%, such as 10%, 15%, 20%, 25%, 30%, 35%, 40%, 45%, 50%, 55%, 60%, 65%, 70%, 75%, 80%, 85%, 90%, 95%, 97%, 98%, or 99%. In specific examples, Lewis acid sites having "at least" a particular percentage of Lewis acid sites include values between, and including, the listed value and 95%. In particular examples, the ratio of Lewis acid sites to Brønsted acid sites is determined by pyridine-adsorption FTIR.

In yet further implementations, the solid catalysts have a surface area of between about 100 $m^2/g$ and about 5000 $m^2/g$, such as between about 300 $m^2/g$ and about 2000 $m^2/g$, between about 500 $m^2/g$ and about 1200 $m^2/g$, or between about 700 $m^2/g$ and about 1000 $m^2/g$. In further examples, the solid catalysts have a surface area of at least about 100 $m^2/g$, such as at least about 300 $m^2/g$, at least about 500 $m^2/g$, at least about 700 $m^2/g$, or at least about 800 $m^2/g$, including between 100 $m^2/g$ and 5000 $m^2/g$, between 300 $m^2/g$ and 2000 $m^2/g$, between 500 $m^2/g$ and 1200 $m^2/g$, or between 700 $m^2/g$ and 1000 $m^2/g$, or at least 100 $m^2/g$, such as at least 300 $m^2/g$, at least 500 $m^2/g$, at least 700 $m^2/g$, or at least 800 $m^2/g$. In specific examples, catalyst surface areas of "at least" a particular value include values between, and including, the listed value and 5000 $m^2/g$. In particular examples, the catalyst has a surface area of 100 $m^2/g$, 200 $m^2/g$, 300 $m^2/g$, 400 $m^2/g$, 500 $m^2/g$, 600 $m^2/g$, 700 $m^2/g$, 800 $m^2/g$, 900 $m^2/g$, 1000 $m^2/g$, 1100 $m^2/g$, 1200 $m^2/g$, 1500 $m^2/g$, 2000 $m^2/g$, 2500 $m^2/g$, 3000 $m^2/g$, 3500 $m^2/g$, 4000 $m^2/g$, 4500 $m^2/g$, or 5000 $m^2/g$.

In additional implementations, the solid catalysts have a mean particle size of between about 0.1 μm and about 100 μm, such as between about 0.3 μm and about 50 μm, or between about 0.5 μm and about 30 μm, including between 0.1 μm and 100 μm, between 3 μm and 50 μm, or between 0.5 μm and 30 μm, such as 0.1 μm, 0.5 μm, 1 μm, 2 μm, 3 μm, 4 μm, 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, or 100 μm. In particular examples, the particle size is determined with reference to the longest side of the particle at the longest point on the side.

In some examples, the solid catalyst is porous and has a mean pore size of between about 1 nm and about 100 nm, such as between about 2 nm and about 50 nm, between about 4 nm and about 30 nm, between about 6 nm and about 20 nm, between about 7 nm and about 13 nm, between about 8 nm and about 12 nm, between about 9 nm and about 11 nm, or between about 9 nm and about 10 nm, including between 1 nm and 100 nm, between 2 nm and 50 nm, between 4 nm and 30 nm, between 6 nm and 20 nm, between 7 nm and 13 nm, between 8 nm and 12 nm, between 9 nm and 11 nm, or between 9 nm and 10 nm, such as 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, or 100 nm. In further examples, porous catalysts have a mean pore size of at least about 7 nm, such as at least about 8 nm, at least about 9 nm, or at least about 10 nm, including at least 7 nm, at least 8 nm, at least 9 nm, or at least 10 nm. In specific examples, catalyst mean pore sizes of "at least" a particular value include values between, and including, the listed value and 100 nm.

Porous catalysts, in particular implementations, have a mean pore volume of between about 0.2 $cm^3/g$ and about 15 $cm^3/g$, such as between about 0.8 $cm^3/g$ and about 1.75 $cm^3/g$, between about 0.9 $cm^3/g$ and about 1.6 $cm^3/g$, between about 1.1 $cm^3/g$ and about 1.5 $cm^3/g$, between about 1.2 $cm^3/g$ and about 1.4 $cm^3/g$, or between about 1.3 $cm^3/g$ and about 1.4 $cm^3/g$, including between 0.2 $cm^3/g$ and 15 $cm^3/g$, between 0.8 $cm^3/g$ and 1.75 $cm^3/g$, between 0.9 $cm^3/g$ and 1.6 $cm^3/g$, between 1.1 $cm^3/g$ and 1.5 $cm^3/g$, between 1.2 $cm^3/g$ and 1.4 $cm^3/g$, or between 1.3 $cm^3/g$ and 1.4 $cm^3/g$, such as 0.2 $cm^3/g$, 0.5 $cm^3/g$, 0.75 $cm^3/g$, 0.8 $cm^3/g$, 0.9 $cm^3/g$, 1 $cm^3/g$, 1.1 $cm^3/g$, 1.2 $cm^3/g$, 1.3 $cm^3/g$, 1.4 $cm^3/g$, 1.5 $cm^3/g$, 1.6 $cm^3/g$, 1.7 $cm^3/g$, 1.75 $cm^3/g$, 1.8 $cm^3/g$, 1.9 $cm^3/g$, 2 $cm^3/g$, 2.5 $cm^3/g$, 3 $cm^3/g$, 3.5 $cm^3/g$, 4 $cm^3/g$, 4.5 $cm^3/g$, 5 $cm^3/g$, 5.5 $cm^3/g$, 6 $cm^3/g$, 6.5 $cm^3/g$, 7 $cm^3/g$, 7.5 $cm^3/g$, 8 $cm^3/g$, 8.5 $cm^3/g$, 9 $cm^3/g$, 9.5 $cm^3/g$, 10 $cm^3/g$, 10.5 $cm^3/g$, 11 $cm^3/g$, 11.5 $cm^3/g$, 12 $cm^3/g$, 12.5 $cm^3/g$, 13 $cm^3/g$, 13.5 $cm^3/g$, 14 $cm^3/g$, 14.5 $cm^3/g$, or 15 $cm^3/g$. In further implementations, the porous catalysts have a mean pore volume of at least about 1.0 $cm^3/g$, such as at least about 1.1 $cm^3/g$, at least about 1.2 $cm^3/g$, or at least about 1.3 $cm^3/g$, including at least 1.0 $cm^3/g$, at least 1.1 $cm^3/g$, at least 1.2 $cm^3/g$, or at least 1.3 $cm^3/g$. In specific examples, catalyst mean pore volumes of "at least" a particular value include values between, and including, the listed value and 15 $cm^3/g$.

The ratio of catalyst to substrate can affect the method 100, including the reaction time, product yield, and product distribution. In particular examples, the ratio of catalyst to substrate is between about 1:200 and about 10:1, such as between about 1:100 and about 2:1, between about 1:50 and about 3:2, between about 1:50 and about 1:1, or between about 1:20 and about 3:20, including between 1:200 and 10:1, between 1:100 and 2:1, between 1:50 and 3:2, between 1:50 and 1:1, or between 1:20 and 3:20, such as 1:200, 1:100, 1:50, 1:20, 3:20, 1:5, 1:1, 3:2, 2:1, or 10:1. In further examples, the ratio of catalyst to substrate is at least about 1:200, such as at least about 1:100, at least about 1:50, at least about 1:20, at least about 1:10, or at least about 1:5, including at least 1:100, at least 1:50, at least 1:20, at least 1:10, or at least 1:5. In more particular examples, listed ratios of catalyst to substrate having "at least" a particular ratio include values between, and including, the listed ratio and 10:1.

In a particular implementation, the catalyst is a metal-doped (or substituted) SBA-15 material, such as Zr-SBA-15. In a particular example, the catalyst is a metal doped SBA-15 material having a ratio of silicon-to-metal (such as silicon-to-zirconium) of between about 10:1 and about 100:1, such as between about 20:1 and about 40:1, including between 10:1 and 100:1 or between 20:1 and 40:1. In particular examples, the catalyst has a ratio of silicon to metal of 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1. The metal doped SBA-15 material can have a mean pore size of between about 7 nm and about 11 nm, such as between about 8 nm and about 10 nm, including between 7 nm and 11 nm or between 8 nm and 10 nm, such as 7 nm, 7.5 nm, 8 nm, 8.5 nm, 9 nm, 9.5 nm, 10 nm, 10.5 nm, or 11 nm. The metal doped SBA-15 material can have an acidity, as measured by temperature-programmed desorption of nitrogen, of between about 0.2 mmol/g $NH_3$ and about 0.8 mmol/g $NH_3$, such as between about 0.6 mmol/g $NH_3$ and about 0.8 mmol/g $NH_3$, including between 0.2 mmol/g $NH_3$ and 0.8 mmol/g $NH_3$ or between 0.6 mmol/g $NH_3$ and 0.8 mmol/g $NH_3$, such as 0.6 mmol/g $NH_3$, 0.625 mmol/g $NH_3$, 0.65 mmol/g $NH_3$, 0.675 mmol/g $NH_3$, 0.7 mmol/g $NH_3$, 0.725 mmol/g $NH_3$, 0.75 mmol/g $NH_3$, 0.775 mmol/g $NH_3$, or 0.8 mmol/g $NH_3$.

In particular embodiments of the present disclosure, the properties of the mesoporous catalyst material can be adjusted during synthesis of the material. For example, when the catalyst is Zr-SBA-15, properties such as the pore size and surface area can be adjusted by altering the hydrothermal synthesis temperature of the material, with higher temperatures generally providing larger pore sizes and lower surface areas. In addition, the degree of metal substitution can be influenced by the amount of source metal present during synthesis.

In some cases, the mesoporous catalyst material can be used in conjunction with a co-catalyst or material that can modify the properties of the mesoporous catalyst material. Halide salts (including salts with F, Cl, Br, or I) of alkali metals (Li, Na, K, Rb, and Cs), including mixtures thereof, in particular aspects, can be added to the catalyst (such as treating the catalyst with the salt prior to adding the catalyst to the reaction mixture, or adding the salt directly to a reaction mixture that includes that catalyst), and can affect the amount or distribution of the reaction products, such as increasing the amount of ester produced by the reaction. Examples of alkali metal halides that can be added to the reaction mixture include LiCl, LiBr, LiI, NaCl, NaBr, NaI, KCl, KBr, KI, and combinations thereof. In particular cases, the reaction (such as a reaction that includes ethanol in the reaction mixture) produces ethyl lactate, and addition of an alkali metal halide increases the production of ethyl lactate.

In specific examples, the reaction mixture includes between about 0.001 wt % (relative to the weight of catalyst) and about 10% of an alkali metal halide, such as between about 0.005 wt % and about 5 wt %, between about 0.005 wt % and about 2.5 wt %, between about 0.005 wt % and about 1 wt %, between about 0.005 wt % and about 0.5 wt %, between about 0.005 wt % and about 0.25 wt %, between about 0.005 wt % and about 0.10 wt %, between about 0.005 wt % and about 0.08 wt %, between about 0.01 wt % and about 5 wt %, between about 0.01 wt % and about 2.5 wt %, between about 0.01 wt % and about 1 wt %, between about 0.01 wt % and about 0.5 wt %, between about 0.01 wt % and about 0.25 wt %, between about 0.01 wt % and about 0.10 wt %, or between about 0.01 wt % and about 0.08 wt %, such as between 0.005 wt % and 5 wt %, between 0.005 wt % and 2.5 wt %, between 0.005 wt % and 1 wt %, between 0.005 wt % and 0.5 wt %, between 0.005 wt % and 0.25 wt %, between 0.005 wt % and 0.10 wt %, between 0.005 wt % and 0.08 wt %, between 0.01 wt % and 5 wt %, between 0.01 wt % and 2.5 wt %, between 0.01 wt % and 1 wt %, between 0.01 wt % and 0.5 wt %, between 0.01 wt % and 0.25 wt %, between 0.01 wt % and 0.10 wt %, or between 0.01 wt % and 0.08 wt %. In more specific examples, potassium chloride is included in the reaction mixture in an amount recited in the preceding sentence.

As described above, in step 130, the reaction is carried out in the presence of an alcohol. Suitable alcohols include alcohols having between 1 and 15 carbon atoms, particularly alkyl alcohols having between 1 and 15 carbon atoms. In particular examples, the alcohol is selected from methanol, ethanol, n-propanol, iso-propanol, n-butanol, sec-butanol, iso-butanol, and tert-butanol. If desired, mixtures of alcohols may be used.

In particular implementations, the organic feedstock is converted to organic products that include esters. In a particular example, such as when the feedstock includes a polymeric carbohydrate, such as cellulose, the ester can be an alkyl lactate. In such implementations, the alcohol may be selected based on the ester desired. In some cases, the alcohol can be an alkyl alcohol, with the alkyl group serving as the alkyl group of the alkyl lactate. For example, if a methyl ester is desired, the alcohol may include methanol.

Typically, the alcohol is provided in stoichiometric excess with respect to the organic feedstock. In various implementations, the weight ratio of alcohol to feedstock is between about 5:1 and about 1000:1, such as between about 10:1 and about 750:1, between about 25:1 and about 500:1, or between about 50:1 and about 250:1, including between 5:1 and 1000:1, between 10:1 and 750:1, between 25:1 and 500:1, or between 50:1 and 250:1, such as 5:1, 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1, or 1000:1. In further implementations, the weight ratio of alcohol to carbohydrate feedstock is at least about 5:1, such as at least about 10:1, at least about 25:1, at least about 50:1, at least about 75:1, at least about 100:1, at least about 150:1, at least about 200:1, or at least about 500:1, including at least 5:1, at least 10:1, at least 25:1, at least 50:1, at least 75:1, at least 100:1, at least 150:1, at least 200:1, or at least 500:1. In specific examples, catalyst weight ratios of alcohol to feedstock recited as being "at least" a particular ratio refer to ratios having increasing amounts of feedstock compared with the listed value, including values between, and including, the listed ratio and 5:1.

In some implementations, the alcohol includes additional solvents or reagents. In a specific example, the alcohol is an alcohol-water mixture having between about 0.1 wt % water and about 90 wt % water, such as between about 0.25 wt % water and about 50 wt % water, between about 0.5 wt % water and about 25 wt % water, between about 1 wt % water and about 15 wt % water, between about 2 wt % water and about 10 wt % water, between about 1 wt % water and about 7 wt % water, or between about 2 wt % water and about 6 wt % water, including between 0.1 wt % water and 90 wt % water, between 0.25 wt % water and 50 wt % water, between 0.5 wt % water and 25 wt % water, between 1 wt % water and 15 wt % water, between 2 wt % water and 10 wt % water, between 1 wt % water and 7 wt % water, or between 2 wt % water and 6 wt % water, such as 0.1 wt % water, 0.25 wt % water, 0.5 wt % water, 0.75 wt % water, 1 wt % water, 2 wt % water, 3 wt % water, 4 wt % water, 5 wt % water, 6 wt % water, 7 wt % water, 8 wt % water, 9 wt % water, 10 wt % water, 15 wt % water, 20 wt % water, 25 wt % water, 30 wt % water, 35 wt % water, 40 wt % water, 45 wt % water, 50 wt % water, 55 wt % water, 60 wt % water, 65 wt % water, 70 wt % water, 75 wt % water, 80 wt % water, 85 wt % water, or 90 wt % water. In further implementations, the alcohol-water mixture includes at least about 0.25 wt % water, such as at least about 0.5 wt % water, at least about 1 wt % water, at least about 2 wt % water, at least about 3 wt % water, at least about 4 wt % water, at least about 5 wt % water, at least about 10 wt % water or at least about 20 wt % water, including at least 0.25 wt % water, at least 0.5 wt % water, at least 1 wt % water, at least 2 wt % water, at least 3 wt % water, at least 4 wt % water, at least 5 wt % water, at least 10 wt % water, or at least 20 wt % water. In specific examples, alcohol-water mixtures listed as including "at least" a particular percentage of water include values between, and including, the listed value and 90%.

The reaction time in step 130 is typically selected to be between that resulting in a desired level of product (such as lactic acid ester) formation and when a negligible additional amount of product is formed. In various examples, the reaction is carried out for a period of between about 30 seconds and about 48 hours, such as between about 30 seconds and about 24 hours, between about 15 minutes and about 12 hours, between about 30 minutes and about 10 hours, between about 1 hour and about 10 hours, between about 2 hours and about 8 hours, between about 2 hours and about 6 hours, or between about 2 hours and about 4 hours, including between 30 seconds and 48 hours, between 30 seconds and 24 hours, between 15 minutes and 12 hours, between 30 minutes and 10 hours, between 1 hour and 10 hours, between 2 hours and 8 hours, between 2 hours and 6 hours, or between 2 hours and 4 hours, such as 30 seconds, 45 seconds, 60 seconds, 90 seconds or 2 minutes, 3 minutes, 4 minutes, 5 minutes, 6 minutes, 7 minutes, 8 minutes, 9 minutes, 10 minutes, 15 minutes, 30 minutes, 45 minutes, or 60 minutes, or 2 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, or 48 hours. In further examples, the reaction time is at least about 30 seconds, at least about 2 minutes, at least about 5 minutes, at least about 15 minutes, at least about 30 minutes, at least about 1 hour, at least about 2 hours, at least about 3 hours, at least about 4 hours, at least about 5 hours, or at least about 6 hours, including at least 30 seconds, at least 2 minutes, at least 5 minutes, at least 15 minutes, at least 30 minutes, at least 1 hour, at least 2 hours, at least 3 hours, at least 4 hours, at least 5 hours, or at least 6 hours. In specific examples, reaction times of "at least" a particular value include values between, and including, the listed value and 48 hours.

The reaction temperature may be selected based on a number of factors, including the alcohol and feedstock used, the products desired, and the desired reaction time. In at least some implementations, higher reaction temperatures require shorter reaction times to achieve a similar level of product formation. In addition, higher temperatures may assist in depolymerizing biopolymers in a feedstock. In particular implementations, the reaction temperature is between about 140° C. and about 400° C., such as between about 160° C. and about 350° C., between about 200° C. and about 400° C., between about 200° C. and about 350° C., between about 200° C. and about 300° C., between about 220° C. and about 275° C., between about 230° C. and about 265° C., between about 220° C. and about 300° C., between about 240° C. and about 300° C., or between about 240° C. and about 260° C., including between 140° C. and 400° C., between 160° C. and 350° C., between 200° C. and 400° C., between 200° C. and 350° C., between 200° C. and 300° C., between 220° C. and 275° C., between 230° C. and 265° C., between 220° C. and 300° C., between 240° C. and 300° C., or between 240° C. and 260° C., such as 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., 305° C., 310° C., 315° C., 320° C., 325° C., 330° C., 335° C., 340° C., 345° C., 350° C., 355° C., 360° C., 365° C., 370° C., 375° C., 380° C., 385° C., 390° C., 395° C., or 400° C. In further implementations, the reaction temperature is at least about 140° C., such as at least about 160° C., at least about 175° C., at least about 200° C., at least about 220° C., at least about 240° C., or at least about 260° C., including at least 140° C., at least 160° C., at least 175° C., at least 200° C., at least 220° C., at least 240° C., or at least 260° C. In specific examples, reaction temperatures of "at least" a particular value include values between, and including, the listed value and 400° C.

In yet further implementations, the reaction temperature is selected to be about, or greater than, the critical temperature for the alcohol or alcohol mixture used for the reaction. As used herein, the "critical point" for a substance (which may include mixtures of substances) is the end point on a phase equilibrium curve where the phase boundary between the two phases vanishes. For example, at temperatures higher than the critical temperature, and pressures higher than the critical pressure, a substance may simultaneously be described as a gaseous phase material or a supercritical fluid. As opposed to below the critical temperature and pressure, above the critical temperature and pressure the material can be treated as not having separate, coexisting liquid and vapor phases.

As used herein, "subcritical" means a substance having a combination of temperature and pressure that result in the substance being below the critical point, but comparatively close to the critical point. In various examples, "subcritical" substances have a temperature that is at least about 70% of the critical temperature, but less than the critical temperature, such as temperatures that are at least about 75%, at least about 80%, at least about 85%, at least about 90%, at least about 95%, or at least about 99% of the critical temperature, including at least 70%, at least 75%, at least 80%, at least 85%, at least 90%, at least 95%, or at least 99% of the critical temperature, such as 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the critical temperature. In specific examples, reaction temperatures of "at least" a particular value of the critical temperature include values between, and including, the listed value and 99%. In more specific examples, the pressure of a subcritical substance is between about 50% and about 400% of the critical pressure, such as between about 75% and about 200%, between about 90% and about 150%, between about 80% and about 150%, or between about 70% and about 130% of the critical pressure, including between 50% and 400% of the critical pressure, between 75% and 200%, between 90% and 150%, between 80% and 150%, or between 70% and 130% of the critical pressure, such as 50%, 55%, 60%, 65%, 70%, 75%, 80%, 85%, 90%, 95%, 100%, 125%, 130%, 150%, 175%, 200%, 225%, 250%, 275%, 300%, 325%, 350%, 375%, or 400% of the critical pressure.

In various examples, the reaction temperature is substantially the supercritical temperature for the particular alcohol or alcohol mixture used for the reaction, such as at least about 70%, at least about 75%, at least about 80%, at least about 85%, at least about 95%, or at least about 99% of the supercritical temperature, including at least 70%, at least 75%, at least 80%, at least 85%, at least 95%, or at least 99% of the supercritical temperature, such as 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the supercritical temperature. In specific examples, reaction temperatures of "at least" a particular value of the supercritical temperature include values between, and including, the listed value and 99%.

In further examples, the reaction is carried out under supercritical conditions. The reaction temperature may be a temperature that is equal to or greater than the critical temperature. In various examples, the temperature is at least about 100%, at least about 105%, at least about 110%, at least about 115%, at least about 125%, at least about 150%, or at least about 200% of the critical temperature, including at least 100%, at least 105%, at least 110%, at least 115%, at least 125%, at least 150%, or at least 200% of the critical temperature, such as 100%, 105%, 110%, 115%, 120%, 125%, 130%, 135%, 140%, 145%, 150%, 155%, 160%, 165%, 170%, 175%, 180%, 185%, 190%, 195%, or 200% of the supercritical temperature. In specific examples, reaction temperatures of "at least" a particular value of the critical temperature include values between, and including, the listed value and 200%. In such examples, the pressure may be at least about the critical pressure, such as at least about 100%, at least about 105%, at least about 110%, at least about 115%, at least about 125%, at least about 150%, or at least about 200% of the critical pressure, including at least 100%, at least 105%, at least 110%, at least 115%, at least 125%, at least 150%, or at least 200% of the critical pressure, such as 100%, 105%, 110%, 115%, 120%, 125%, 130%, 135%, 140%, 145%, 150%, 155%, 160%, 165%, 170%, 175%, 180%, 185%, 190%, 195%, or 200% of the critical pressure. In specific examples, reaction pressures of "at least" a particular value of the critical pressure include values between, and including, the listed value and 200%.

In certain implementations, the reaction is carried out in a closed system so that the reaction maintains the critical temperature and pressure of the alcohol or alcohol mixture used for the reaction. In other implementations, the reaction is carried out under other suitable conditions to maintain the critical temperature and pressure of the alcohol or alcohol mixture used for the reaction. In particular examples, the reaction environment is subject to external pressure. For example, the reaction chamber or vessel may be pressurized at the start of, or during, reaction. In particular examples, a pressure of between about 50 psi and about 2000 psi is applied, such as between about 100 psi and about 1000 psi, between about 200 psi and about 700 psi, between about 300 psi and about 600 psi, or between about 350 psi and about 450 psi, including between 50 psi and 2000 psi, between 100 psi and 1000 psi, between 200 psi and 700 psi, between 300 psi and 600 psi, or between 350 psi and 450 psi, such as 50 psi, 75 psi, 100 psi, 150 psi, 200 psi, 250 psi, 300 psi, 350 psi, 400 psi, 450 psi, 500 psi, 550 psi, 600 psi, 650 psi, 700 psi, 750 psi, 800 psi, 850 psi, 900 psi, 950 psi, 1000 psi, 1050 psi, 1100 psi, 1150 psi, 1200 psi, 1250 psi, 1300 psi, 1350 psi, 1400 psi, 1450 psi, 1500 psi, 1550 psi, 1600 psi, 1650 psi, 1700 psi, 1750 psi, 1800 psi, 1850 psi, 1900 psi, 1950 psi, or 2000 psi. In some implementations, the pressure is achieved by charging the reaction chamber or vessel with an inert gas, such as nitrogen, argon, or helium.

If desired, catalyst from method 100 can be reused for additional, subsequent reactions. In some implementations, the catalyst is reused without regeneration. In other implementations, the catalyst is regenerated, such as between each reaction or periodically. In a particular example, the catalyst is regenerated by being calcined, such being calcined in the present of an air stream.

EXAMPLE 1

Production of Ethyl Lactate from Carbohydrates Using Mesoporous Zr-SBA-15

The selective conversion of cellulose, the most abundant and non-edible biomass, as the renewable carbon resource for the production of value-added chemicals could play an important role in a sustainable economy. Among biobased chemicals, ethyl lactate (EL) has potential to be an environmentally benign solvent that might be used to replace petroleum-based toxic halogenated organic solvents. EL can be derived from lactic acid (LA) and ethanol, which are both renewable chemical materials typically made from fermentation of sugars originally from corn. As a commercial "green" solvent, EL works in numerous chemical applications, such as a photoresist carrier solvent, edge-bead remover, and clean-up solvent for semiconductor manufacture.

Fermentation processes can suffer from large amounts of waste products, costly separation, and inability to utilize cellulose without expensive pretreatment. Chemo-catalytic processes can utilize a variety of cellulosic biomass that are not competing with food. Various polyols and simple sugars, e.g., glycerol, xylose and glucose, may be converted to LA and its ester derivatives with heterogenous catalysts. Lewis acid catalyzed retro-aldol condensation is typically a key step to synthesize LA from C5 and C6 sugars.

In contrast, direct use of cellulose to produce LA at high yields is typically only seen with homogenous catalysts. However, homogenousy catalytic processes often face similar separation challenges as fermentative processes.

While $ZrO_2$ may act as a stable catalyst for the synthesis of LA from hemicellulose in hydrothermal media, LA yields are typically relatively low (up to 25% and 18% carbon yields from xylose and xylan, respectively). This may be due to $ZrO_2$ having mixed weak acid/base and redox properties that limit the selectivity to LA. Incorporating Zr into charge-neutral silica framework, in which Zr is less coordinated, may enhance Lewis acidity.

SBA-15 is a mesoporous silica material with properties such as highly ordered mesopore, thick wall, high surface area, and large pore size (5-30 nm), which can allow large biomass molecules to diffuse in and out. Thus, Zr-containing SBA-15 may have stronger Lewis acidity than $ZrO_2$. Weak Brønsted acid sites may facilitate cellulose hydrolysis and subsequently, while strong Lewis acid sites may lead to the conversion of glucose to EL. All these conversion steps can occur in a "one-pot" process. However, one potential challenge associated with the use of solid Lewis acids is their potential instability in the presence of water. However, in alcohol solvents, Lewis acidity of solid catalysts is often retained. The present Example describes the direct conversion of cellulose to EL using mesoporous Zr-SBA-15 catalysts in supercritical ethanol-water solvents.

Figure 4:
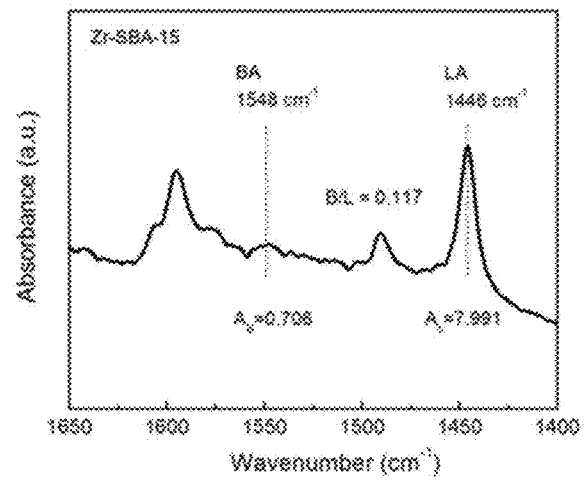
FIG. 4 is a FTIR spectra (absorbance versus wavenumber ($cm^{-1}$)) for pyridine adsorbed on Zr-SBA-15.
Figure 5:
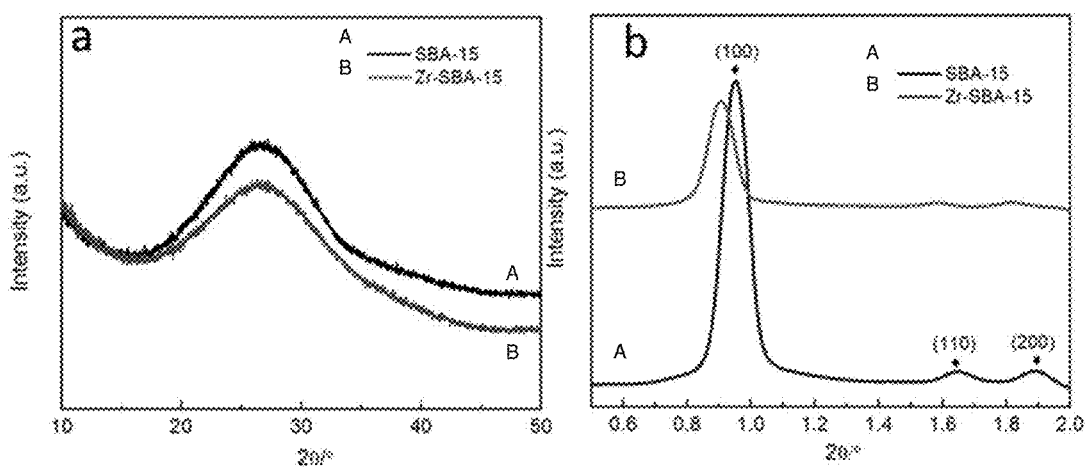
FIG. 5 presents (a) powder XRD patterns of SBA-15 and Zr-SBA-15; and (b) powder XRD small-angle X-ray scatter spectra of SBA-15 and Zr-SBA-15.

FIG. 2 illustrates the spectra of ammonia temperature programmed desorption ($NH_3$-TPD) of Zr-SBA-15 samples, with the calculated total acidity listed in FIG. 3. Pure SBA-15 silica did not show any appreciable ammonia adsorption (only 0.02 mmol $NH_3$/g). The $ZrO_2$ sample showed a weak acidity of 0.30 mmol $NH_3$/g, while the Zr-SBA-15 sample presented the highest acidity of 0.72 mmol $NH_3$/g. Furthermore, the FTIR spectra of pyridine adsorbed on the Zr-SBA-15 distinguished the Lewis acidic (LA) and Brønsted acidic (BA) sites, as shown in FIG. 4. The prominent adsorption bands at 1440 and 1581 $cm^{-1}$ were assigned to the Lewis acid (L) sites, whereas the weak adsorption band at 1481 $cm^{-1}$ was attributed to a combination of Brønsted and Lewis acid (B+L) sites. A very weak band at 1541 $cm^{-1}$ was observed, which typically corresponds to the Brønsted acid sites. The relative density of Brønsted/Lewis acid sites (B/L) was 0.117, obtained from the bands at 1541 $cm^{-1}$ and 1440 $cm^{-1}$ after normalizing the peak areas with the respective molar extinction coefficients. These results indicated that the Zr-SBA-15 sample contained predominantly strong Lewis acid sites, as well as weak Brønsted acid sites. In addition, the mesoporous structure of the Zr-SBA-15 silicate was demonstrated by powder XRD and small-angle X-ray scattering (SAXS) (FIG. 5). TEM images indicated that the pore size of the Zr-SBA-15 was approximately 9 nm, as shown in FIG. 6.

FIG. 7 compares the yields of the main products formed from reacting cellulose with different catalysts, solvents, and feed loadings. The catalytic effect of Zr-SBA-15 was obvious for promoting the yield of EL. Neither the commercial $ZrO_2$ nor the pure SBA-15 silica resulted in the high yields of EL (8.2% and 5.1%, respectively), while EL yield increased to ~30% over the Zr-SBA-15 catalyst after reacting microcrystalline cellulose at 260° C. for 6 hours in ethanol-water solvent (95% ethanol, 5% water). In a control reaction without added catalyst, the EL yield was ~2.1%. Without catalyst, or with the pure SBA-15, noticeable amounts of HMF and furfural were produced. Higher yields of ethyl acetals or esters of C2 and C4 compounds, such as acetaldehyde diethyl acetal (ADA) and ethyl 2-hydroxybutanoate (EHB), were obtained over the Zr-SBA-15 than over either $ZrO_2$ or SBA-15. These results suggest that the strong Lewis acidity of the Zr-SBA-15 is a factor that promotes the conversion of cellulose to EL.

One potential difficulty in cellulose conversion is the recalcitrance of cellulose to depolymerization. In the disclosed "one-pot" process, multiple factors enable the selective conversion of cellulose to EL. The use of 5% water in a supercritical ethanol-water mixture solvent (FIG. 7 entries 1-6) weakens the intra-molecular hydrogen bonds responsible for the robustness of cellulose and thus decreases the crystallinity of cellulose until dissolution. $Zr^{4+}$ metal centers with empty d orbitals in the framework serve as water-tolerant Lewis acid sites, and the limited hydrophobic property of silica may stabilize the $Zr^{4+}$ Lewis acidic sites inside the pores of the SBA-15 silica in the presence of 5 wt % water. However, in subcritical water, only a trace amount of lactic acid (1.4%) was produced, while HMF (14.6%) and levulinic acid (20.9%) were the main products (FIG. 7, entry 7), implying that the Lewis acidity of Zr-SBA-15 was lost. The transformation of cellulose to EL was completed in supercritical ethanol-water mixtures at moderate temperatures and pressures, which are sufficient for the depolymerization of cellulose and more compatible with stabilizing the solid Lewis acid Zr-SBA-15 catalyst.

Cellulose loading affected the yield of EL to a lesser extent. With increasing the cellulose loading from 1 wt % to 10 wt %, and keeping a constant mass ratio of cellulose to catalyst, the EL yield decreased from ~30% to ~25%, while the yield of solid residue increased from ~8.6% to ~34%. The solid residue included unreacted cellulose and re-polymerized humins, thus longer reaction times would likely be needed at higher loadings of cellulose.

Figures 8, 9:
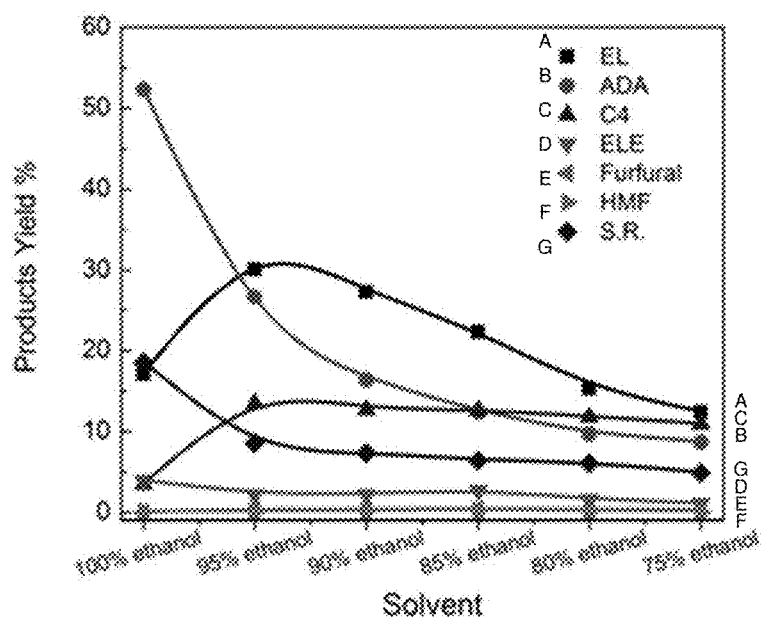
FIG. 8 is a table listing the critical conditions of ethanol-water solutions at different ethanol-to-water ratios.
FIG. 9 is a graph of liquid-phase product yield (%) from cellulose conversion with Zr-SBA-15 catalyst versus wt % ethanol for various ethanol-water solutions.

To further understand the role of water in ethanol, anhydrous ethanol, and ethanol-water mixture solutions at different water-to-ethanol ratios were used under super- and sub-critical conditions. The critical conditions of ethanol-water solutions are shown in FIG. 8. The water content in the ethanol-water solutions significantly affects the EL yield. As shown in FIG. 9, in supercritical anhydrous ethanol, the yield of EL from cellulose was ~17% after reacting for 6 hours at 260° C. (at 400% psi $N_2$ initial pressure, 0.2 g cellulose, and a 1:2 mass ratio of catalyst to cellulose), while by adding 5% water, the EL yield almost doubled (~30%) under otherwise identical conditions. The yield of solid residue (here, an indicator of unreacted cellulose) decreased significantly from ~20% to ~8% with adding 5% water to the pure ethanol solvent, suggesting that water facilitates cellulose deconstruction. Other products included acetaldehyde diethyl acetal (ADA), ethyl 2-hydroxybutanoate (EHB), and ethyl levulinate (ELE).

Comparing the effect of subcritical water to supercritical ethanol on the rate of liquefying lignocellulosic biomass, faster hydrolytic cleavage may be associated with subcritical water, while slower pyrolytic cleavage dominates in supercritical ethanol in the temperature range of 250° C.-350° C. Therefore, adding a small amount of water (5 wt %) in supercritical ethanol may enhance the hydrolytic degradation of cellulose, leading to faster depolymerization of cellulose. On the other hand, in supercritical alcohol, the repolymerization of cellulose-degraded intermediates may be suppressed due to the reactions between ethanol and biomass intermediates such as aldehydes, carboxylic acids, ketones, etc. Therefore, faster depolymerization of cellulose and slower recombination of intermediates in the ethanol-water mixture solvents (up to 15 wt % water) may enhance the yields of EL. However, the EL yield reached a maximum as the proportion of water was 5 wt %. Further increasing the ratio of water to ethanol decreased the EL yield.

A higher water proportion in the solvent may produce two consequences: deactivating the Lewis acid sites and increasing the critical temperature of the mixed solvent. The deactivation of Lewis acid sites caused by water adsorption can lead to the transformation of a Lewis acid to a Brønsted acid. When the water proportion was >20 wt %, the critical temperature of the ethanol-water mixture was >260° C. However, no distinct difference of product distribution was observed between the supercritical solvent containing 15 wt % water and the subcritical solvent with 25 wt % water.

Thus, the inhibitive effect of water on the Lewis acid sites, instead of the change of the ethanol-water solvent states, may be the primary factor causing the decreased yield of EL with increasing water content in the ethanol-water mixtures (>5 wt % water).

To optimize the yield of EL, cellulose was converted in an ethanol-water mixture containing 5 wt % water at different process conditions for two-hour reactions using 400 psi of $N_2$ initial pressure, 0.2 g substrate, and 0.15 g catalyst. As shown in FIGS. 10 and 11, varying the temperature has a pronounced effect on the yield of EL. Below 200° C., cellulose did not show appreciable conversion. At 240° C. (subcritical condition), the highest yield of 25.4% was achieved after a 10-hour reaction. At 250° C. (near-critical condition), ~30% EL was produced, yet it took 6 hours to plateau. While at 260° C. (supercritical condition), after 2 hours, the yield of EL varied little and reached the maximum observed yield of 30.3%. Similarly, the yields of ADA, EHB, and ethyl levulinate (ELE) consistently increased with extending reaction time. Conversely, the HMF and furfural yields consistently decreased with increasing reaction time.

Brønsted acids can hydrolyze cellulose to glucose, followed by the dehydration of glucose to HMF. Thus, the co-existence of furfural, HMF, and EL in the final products indicates that the Lewis acid and Brønsted acid sites co-existed on the Zr-SBA-15 catalyst. Of particular note is the fact that HMF and furfural almost completely vanished after reaction for 4 hours at 260° C. Higher temperatures led to the transformation of HMF and furfural to ELE through a Brønsted acid catalyzed rehydration and a transfer hydrogenation reaction promoted by Lewis acid, respectively. Notably, the solid residue decreased steadily with reaction time, indicating that the conversion of cellulose increased.

Figure 12:
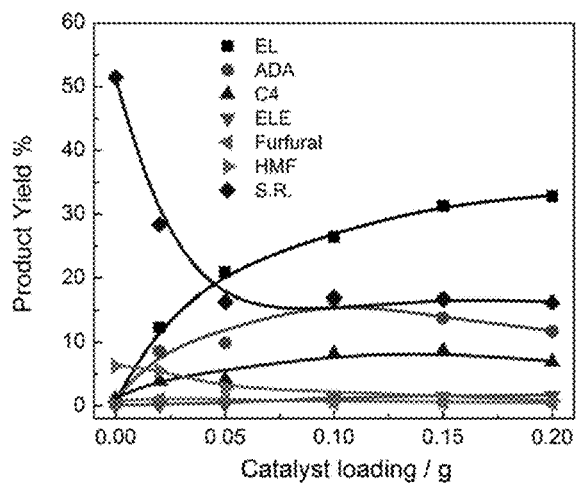
FIG. 12 is a graph of product yield (%) versus Zr-SBA-15 catalyst loading (g) for the conversion of 0.2 g cellulose in 20 g of an ethanol-water (95 wt % ethanol and 5 wt % water) at 260° C. for 2 hours at an initial pressure of 400 psi $N_2$.

The effect of different catalyst loading amounts on the conversion of cellulose is depicted in FIG. 12. The yield of EL showed a steady uptrend as the catalyst loading increased, reaching ~33% as the mass ratio of catalyst to cellulose was 1:1. The yield of ELE also increased steadily with increasing the catalyst loading, but was lower than that of EL. The yields of ADA and EHB increased first with increased catalyst loading, and then decreased as the catalyst-to-cellulose ratio was higher than 0.5. The yields of HMF and furfural consistently decreased as the catalyst loading increased.

Figure 13:
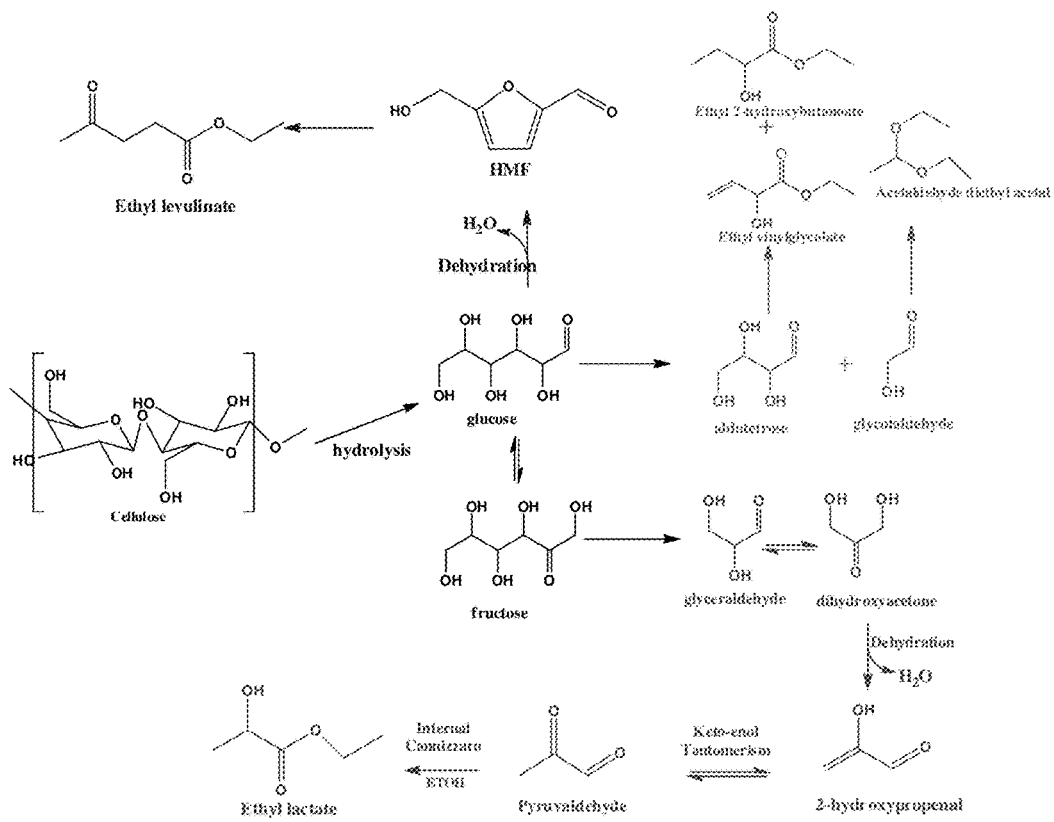
FIG. 13 illustrates a proposed reaction mechanism for the conversion of cellulose to ethyl lactate in ethanol solvent with Zr-SBA-15 catalyst.

The reaction pathway of converting cellulose to EL over Zr-SBA-15 catalyst may begin at the hydrolytic/pyrolytic deconstruction of cellulose, as shown in FIG. 13. Cellulose decomposed to glucose, which was then isomerized to fructose. The $Zr^{4+}$ ions, as the Lewis acid sites, interacted with the carbonyl group of fructose, breaking it down to glyceraldehyde and dihydroxyacetone via retro-aldol condensation. Glyceraldehyde underwent the dehydration to form 2-hydroxypropenal, then to pyruvaldehyde through keto-enol tautomerization, and finally to EL in ethanol solvent. Glucose might also lead to one C4 fragment of aldo-tetrose and another C2 piece of glycolaldehyde, which are the precursors of C4 and C2 acid ester products.

Figure 10A:
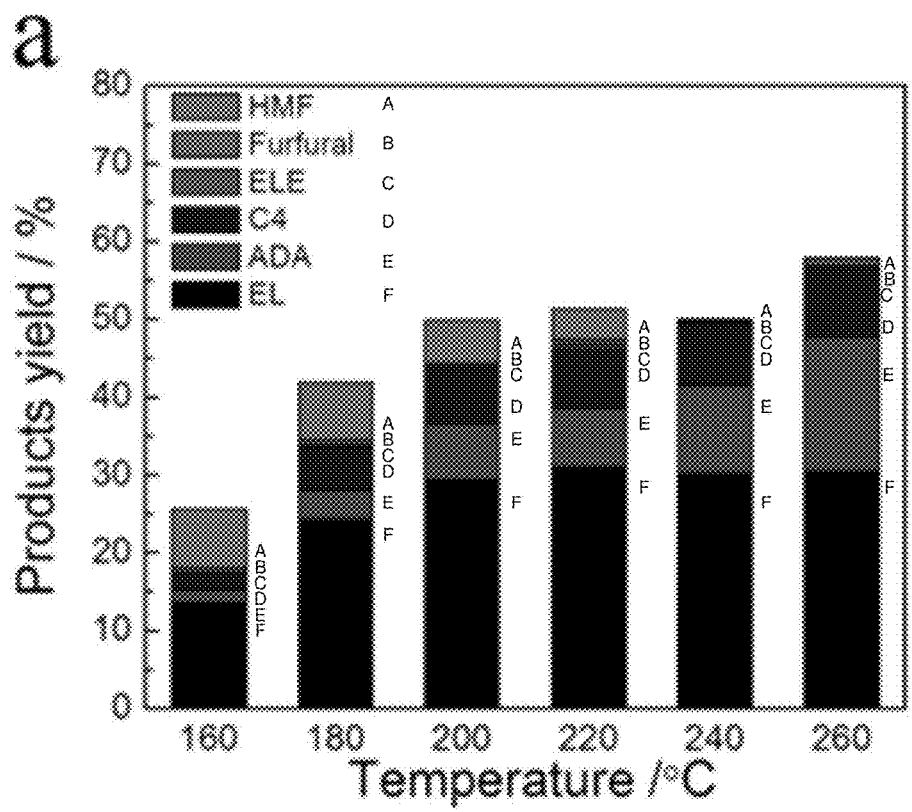
FIG. 10A presents a graph of product yield versus reaction temperature (° C.) for glucose conversion catalyzed by Zr-SBA-15 catalyst.
Figure 10B:
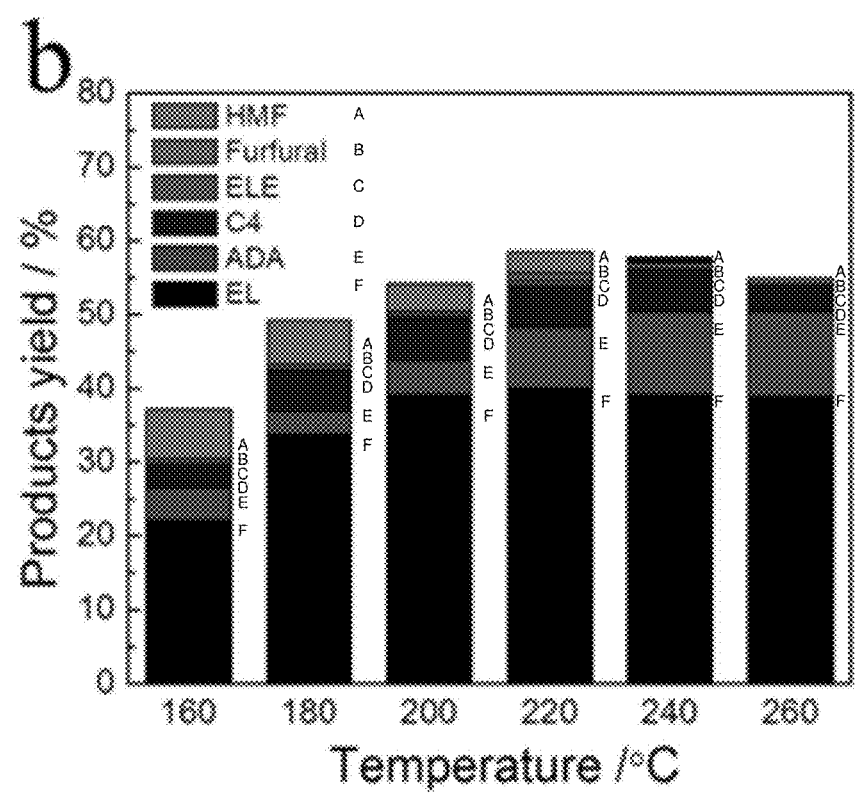
FIG. 10 B presents a graph of product yield versus reaction temperature (° C.) for fructose conversion catalyzed by Zr-SBA-15 catalyst.
FIG. 10C presents a graph of product yield versus reaction temperature (° C.) for cellulose conversion catalyzed by Zr-SBA-15 catalyst.
FIG. 10D presents a graph of solid residue (%) remaining after conversion of glucose, fructose, and cellulose catalyzed by Zr-SBA-15 versus reaction temperature (° C.).
Figure 10C:
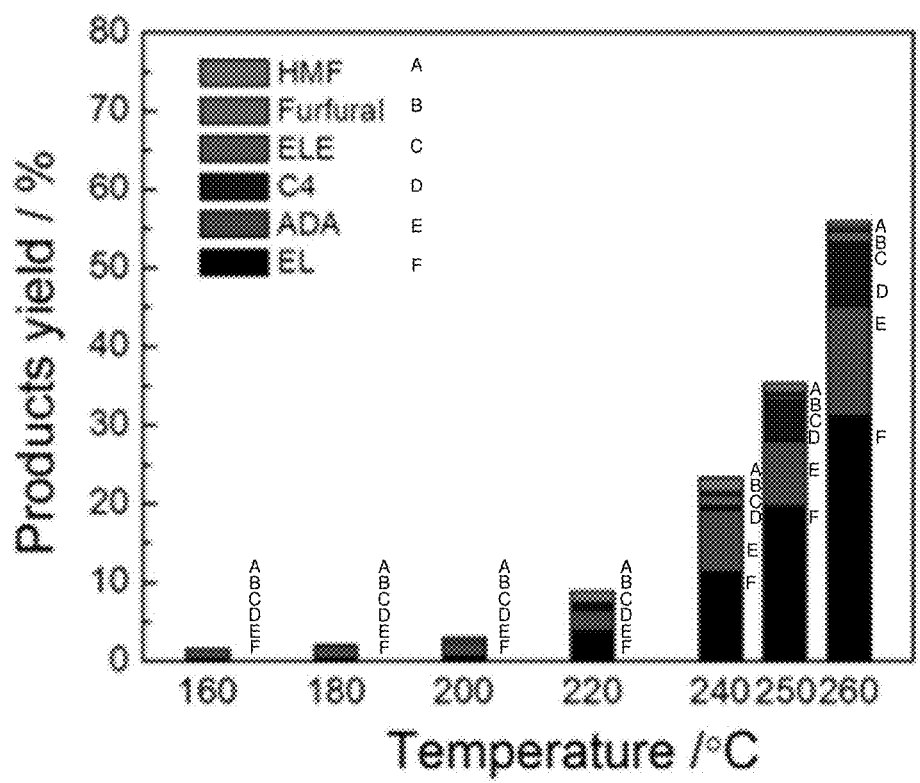
Figure 10D:
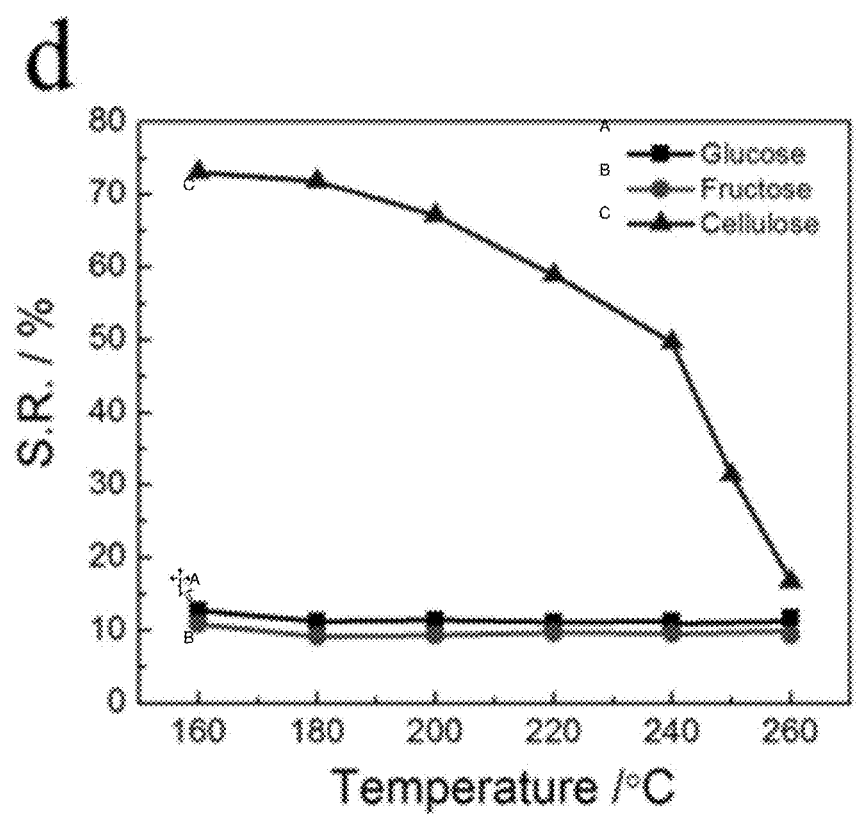
Figure 11:
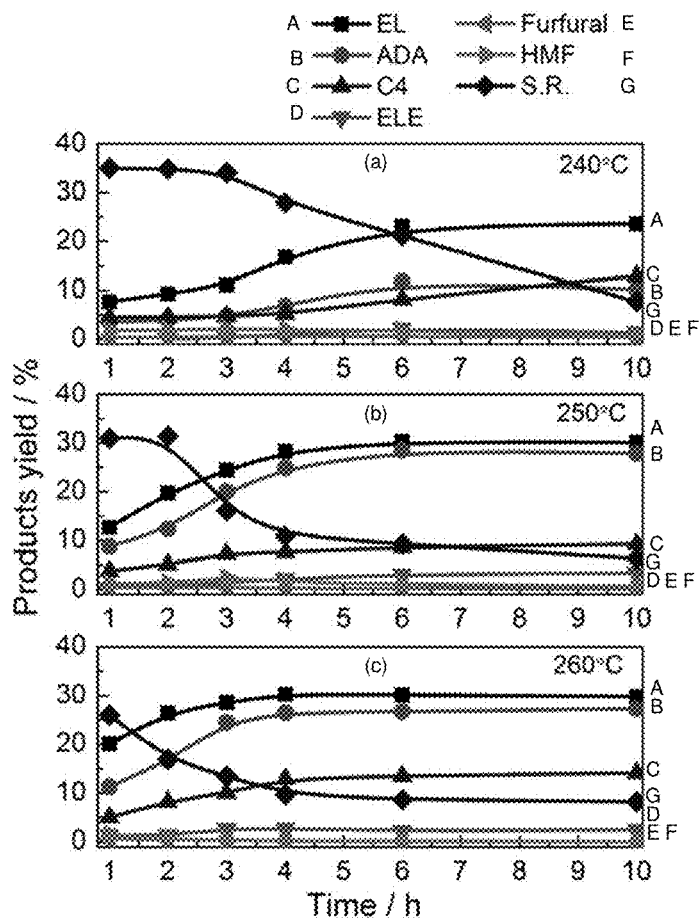
FIG. 11 is graphs of product yield (%) versus reaction time (hours) for cellulose conversion reactions carried out at 240° C. (a), 250° C. (b), and 260° C. (c) using 0.1 g Zr-SBA-15 catalyst, 20 g of a 95 wt % ethanol, 5% water ethanol-water mixture, 0.2 g cellulose, and an initial pressure of 400 psi $N_2$.

To validate the reaction pathway, glucose and fructose were used as the probe reactants (FIGS. 10A and 10B, respectivley). Glucose was readily converted to EL in a ~30% yield at a much lower temperature of 200° C. The yield of EL reached as high as ~40% from fructose. The position of the C—C bond cleavage via retro-aldol condensation of ketohexose and aldohexose led to the different yields of alkyl lactates. Thus the higher yield of EL from fructose is likely due to the preferred disintegration of the carbon bond between the C3 and C4 positions. FIG. 10D shows that at subcritical conditions (≤ 240° C.), the conversion of cellulose was low, which corresponds to the high solid residue yield of 50%-70%, while the solid residue yield decreased sharply at near-critical (250° C.) and supercritical (260° C.) conditions. Thus, the depolymerization of cellulose was likely the rate-limiting step of converting cellulose to EL with the Zr-SBA-15 catalyst.

Figure 14:
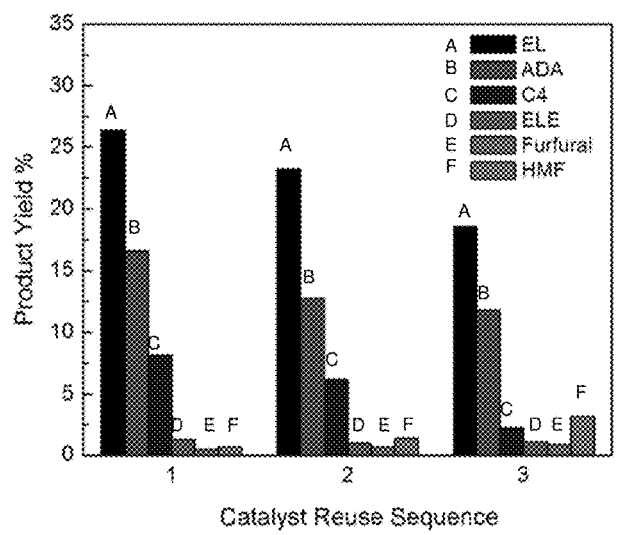
FIG. 14 is a graph of product yield (%) versus the number of reactions run on a particular un-regenerated, spent Zr-SBA-15 catalyst for the conversion of 0.2 g cellulose in 95% ethanol solvent (5% water) at 260° C. for 2 hours using 400 psi initial $N_2$ pressure and 0.1 g catalyst.

The stability of the Zr-SBA-15 catalyst in supercritical ethanol-water solvents was determined. Over three consecutive runs at 260° C., the yield of EL from cellulose steadily decreased when the catalyst was re-used catalyst without regeneration (FIG. 14). These results suggest that re-polymerized humins might inhibit the catalyst's activity. The yields of furfural and HMF increased with increasing the re-use cycles of the catalyst.

Figure 15:
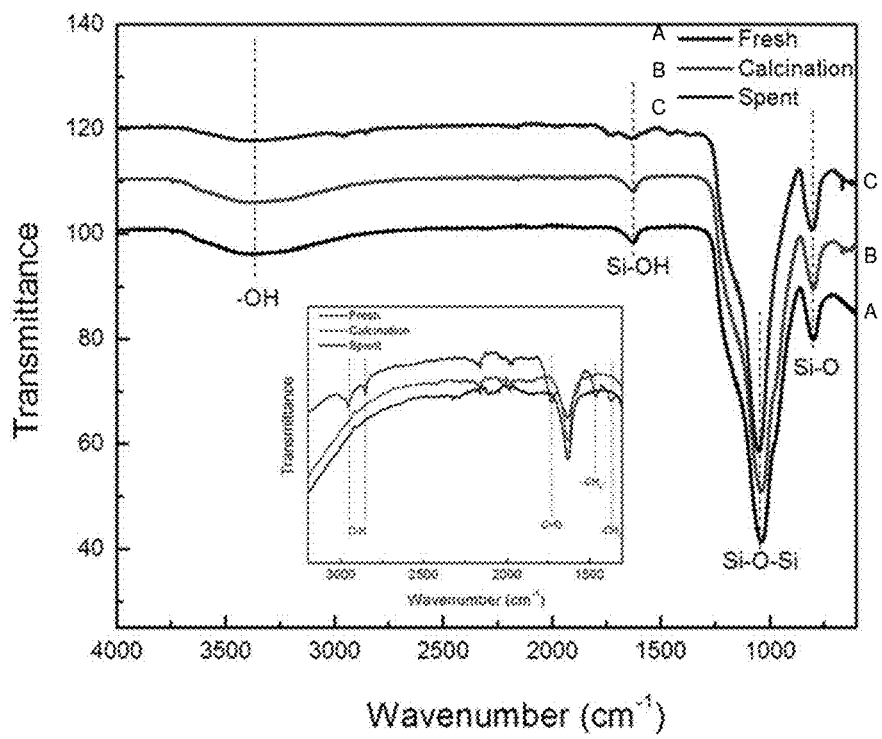
FIG. 15 presents ATR-FTIR spectra (transmittance versus $cm^{-1}$) of fresh, spent (used once and unregenerated), and regenerated (used 5 times then regenerated by calcination) Zr-SBA-15 catalysts for conversion of 0.2 g cellulose at 260° C. for 2 hours and 400 psi starting $N_2$ pressure using 20 g ethanol-water mixture (95 wt % ethanol and 5 wt % water) and 0.1 g catalyst.

Since only the weak Brønsted acid sites on the fresh Zr-SBA-15 catalyst were identified by the pyridine-FTIR characterization, the deposition of the cellulose-derived solid residues on the spent Zr-SBA-15 catalyst apparently changed the surface properties. As shown in FIG. 15, the ATR-FTIR spectra of the spent Zr-SBA-15 catalyst exhibited a broad peak at ~3380 $cm^{-1}$, which is attributed to the stretching —OH band; the peaks at 2960 to 2840 $cm^{-1}$ are the stretching vibration signal of the CH band in —$CH_2$— or —$CH_3$ groups; the peaks located at 1730 $cm^{-1}$ are likely the stretching vibrations of C═O bands in carboxylic acids, and the bands at 1460 and 1360 $cm^{-1}$ likely belong to the —$CH_2$— and —$CH_3$ deformation vibrations. Therefore, carboxylic acid groups on the spent catalyst surface enhanced the Brønsted acidity and led to higher yields of HMF and furfural.

Figure 16:
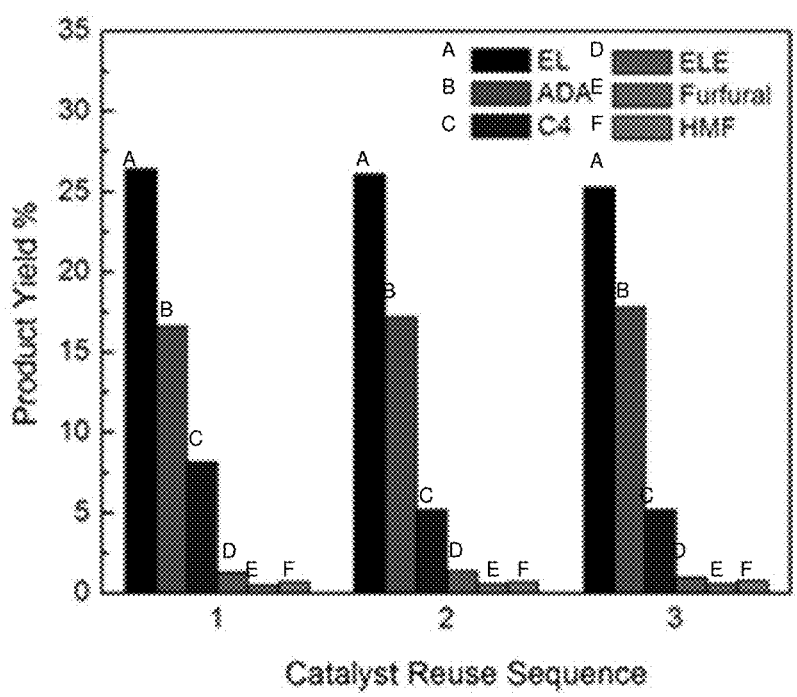
FIG. 16 is a graph of product yield (%) versus the number of catalyst reuses for cellulose conversion (0.2 g) in 95% ethanol solvent (5% water) at 260° C. for 2 hours at 400 psi $N_2$ initial pressure using a 1:2 mass ratio of catalyst to cellulose, with the catalyst being regenerated after each reaction by calcination in flowing air at 550° C. for 6 hours.

The organic solid residues on the spent catalysts can be easily removed by calcination in air flow. According to the FTIR characterization, the regenerated catalyst showed a similar spectra as the fresh catalyst. Correspondingly, after regeneration (calcination at 550° C. for 5 hours), the yield of EL was steady in consecutive runs (FIG. 16). The high-resolution TEM images (FIG. 6) also showed that the structure of the regenerated catalyst was still highly ordered, and the average pore size was unchanged.

Figure 17:
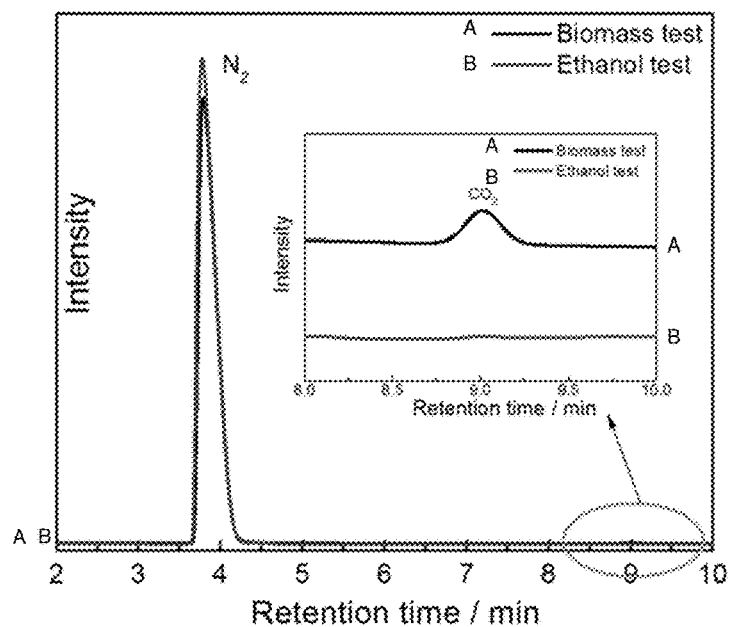
FIG. 17 presents the gas chromatography spectra of the gas phase products from an ethanol-water solvent stability test at 260° C. for 6 hours at a 400 psi initial $N_2$ pressure without a biomass feedstock using 20 g of ethanol-water mixture (95 wt % ethanol and 5 wt % water) and 0.1 g Zr-SBA-15 catalyst separated on a Carbowax column (a) or other columns as described (b).
Figure 18:
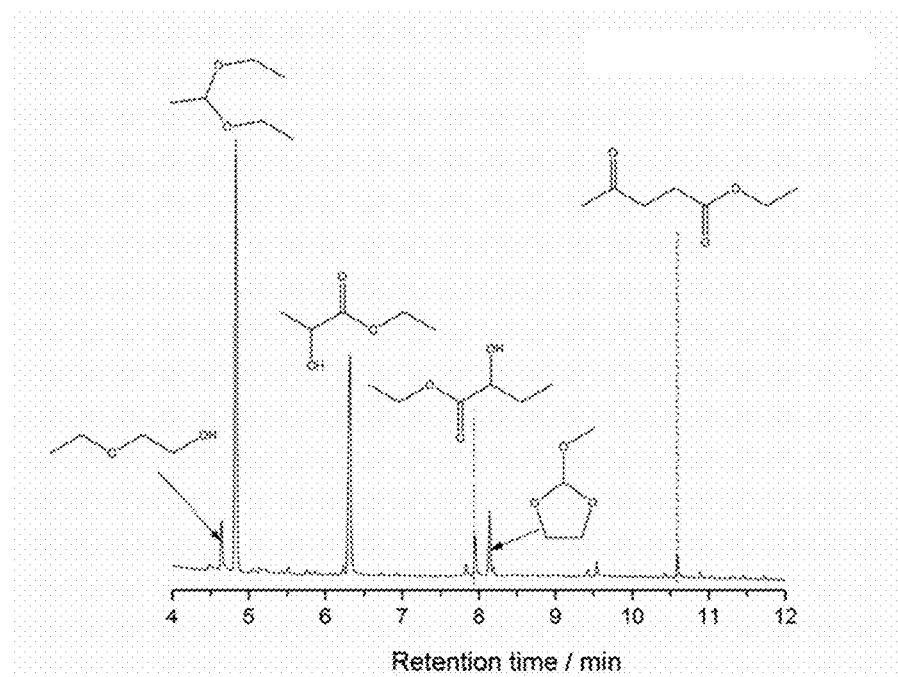
FIG. 18 presents the gas chromatography-mass spectrometry spectra of liquid-phase products from the conversion of cellulose (0.2 g) in an ethanol-water mixture (95 wt % ethanol and 5 wt % water) with 0.1 g of Zr-SBA-15 catalyst for 2 hours at 260° C. and an initial $N_2$ pressure of 400 psi.

In order to test the ethanol solvent stability under this reaction system, a control reaction was conducted. Pure ethanol was reacted with Zr-SBA-15 at 260° C. without any reactant. The gaseous products were analyzed via GC-online system after the reaction. Only nitrogen was observed, without any hydrogen or carbon dioxide, while when cellulose was added, carbon dioxide was detected (FIG. 17), indicating that ethanol as a solvent is stable under this reaction system.

In summary, ethyl lactate was directly produced from cellulose in 95% supercritical ethanol-water solutions with Zr-SBA-15 catalyst. Under the tested conditions, the highest ethyl lactate yield was 33%, while the process without Zr-SBA-15 only yielded negligible ethyl lactate. The addition of a small amount of water in supercritical ethanol, as well as the Brønsted acidity of Zr-SBA-15, can facilitate the hydrolysis of cellulose, which is the initial step of the conversion of cellulose. The Lewis acidity of Zr-SBA-15 will then lead to the conversion of glucose to ethyl lactate by isomerization, retro-aldol condensation, and inter-molecular Cannizzaro reactions. The hydrophobic property of the silica framework can stabilize the majority of the $Zr^{4+}$ Lewis acidic sites in the presence of certain amounts of water; however, excessive water may diminish the Lewis acidity of Zr-SBA-15. Overall, this one-pot process using the Zr-SBA-15 catalyst is an environmentally-friendly method of producing ethyl lactate from cellulose, including non-food cellulose, which has potential to replace the commercial process using food grade corn starch as the raw material.

Materials

The following reagents and products were used as received for this Example: Cellulose microcrystalline, average particle size 50 μm, and cellobiose (98%) were purchased from Acros Organics (Morris Plains, N.J.). Furfural (99%), 5-(Hydroxymethyl) furfural (99%), hydrochloric acid (36.5-38.0%, BioReagent), triblock copolymer Pluronic P123, tetraethyl orthosilicate (>99.0%), n-butanol (>99.0%), and zirconyl chloride octahydrate (98%) were purchased from Sigma Aldrich (St. Louis, Mo.). D(+)-Glucose (Reagent ACS Grade) was purchased from Acros Organics (Morris Plains, N.J.). Ethyl lactate (97%), erythrose syrup (70% w/v), ethyl levulinate (99%), ethyl glycolate (98%), and glycolaldehyde dimethylacetal (98%) were purchased from Alfa Aesar (Ward Hill, Mass.). All materials were used directly without further purification.

Catalyst Preparation

Zr-SBA-15 was synthesized following the procedure described by Chen, et al., "Synthesis of Zr-incorporated SBA-15 Mesoporous Materials in a Self-Generated Acidic Environment," *Chem. Mater.* 16 (2004) 4174-4180, incorporated by reference herein to the extent not inconsistent with the present disclosure. Briefly, 2 g of Pluronic P123 was added to 75 ml of 1.6 M HCl. The mixture was stirred at 40° C. for 3 hours until all P123 dissolved. Next, 4.25 g of TEOS and the appropriate amount of zirconia precursor (the ratio of Si/Zr was 20) were added to the solution and the mixture stirred for another 24 hours at 40° C. The resulting gel was placed in a Teflon-lined autoclave and heated at 100° C. for 24 hours. The solid product was filtered with mild washing, dried at 100° C. overnight, and calcined in flowing air at 550° C. for 6 hours.

Catalyst Characterization:

Small-angle X-ray Scattering (SAXS) was performed using a sample-to-detector distance of 172.1 cm, which provided a two-theta range of approximately 0.3-2.0 degrees. Data was typically collected over 30 seconds at a temperature of 20° C. The x-ray source was Cu Kα radiation with a wavelength of 1.54 Å, which was generated by a Rigaku Ru-200BVH rotating anode. Measurements were made on a Siemens HI-STAR multi-wire area detector (Siemens Analytical X-ray Instruments, Madison, Wis.) and were corrected for background and non-linearities in the detector. Integration of the 2D measurement provided a 1D plot of intensity (arbitrary units) versus the two-theta scattering angle, which was peak-fitted using Material Data Incorporated's JADE.

Transmission electron microscope (TEM) micrographs were captured using a JEOL-JEM 2100F (JEOL USA, Inc., of Peabody, Mass.) operating at 200 kV. The samples were dispersed in 1-butanol, and a drop of the suspension was placed on lacey carbon supported on 300 mesh copper grids.

In a typical $NH_3$ TPD experiment using a Micromeritics AutoChem II 2920 Chemisorption Analyzer (Micrometrics Instrument Corp., of Norcross, Ga.), the catalyst was first degassed in helium at 250° C. for 1 hour, then the temperature decreased to 100° C. with a helium flow. After that, 10% ammonia in helium was absorbed at this temperature for 60 min. 50 mL/min helium was then flowed over the catalyst to remove ammonia gas that was physical adsorbed. Temperature programmed desorption was carried out from 100° C. to 550° C. with a temperature ramp of 10° C./min.

A drift-IR study was performed on an EQUINOX 55 (Bruker Optics Inc., of Billerica, Mass.) equipped with a MCT detector. The samples were degassed at 550° C. for 1 hour under helium in a high temperature reaction chamber containing a Praying Mantis™ diffuse reflection attachment (Harrick Scientific Products, Inc., of Pleasantville, N.Y.). Small aliquots of pyridine were carried by helium and exposed to the sample at room temperature for 15 minutes. Prior to the characterization, the physically adsorbed pyridine was removed from the catalyst by flowing helium over it at 250° C. All spectra were collected at 120° C.

Product Analysis

After reaction, the resultant aqueous phase product samples were prepared for GC-FID, high performance liquid chromatography (HPLC), and gas chromatography coupling with mass spectrometer (GCMS) analysis.

The liquid products (e.g. furfural, HMF) were qualified and quantified by using Shimadzu HPLC (Kyoto, JP). The liquid phase after reaction was filtered through a 0.45 micron syringe filter, and then diluted 10 times with DI water. HPLC analysis was performed using a Shimadzu HPLC system equipped a UV-VIS Detector (Shimadzu SPD 10-AV) and Refractive Index Detector (Shimadzu RID-6A). The samples were separated in an Aminex 87-H column from Bio-Rad (Hercules, Calif.), using 5 mM $H_2SO_4$ as the mobile phase, 0.7 mL/min flow, at a column temperature of 55° C. For quantitative identification and results, the UV-VIS detector was operated at 208 nm and 290 nm.

The liquid products identified in ethanol were qualified and quantified via Agilent GC-MS (Agilent Technologies, Inc., Santa Clara, Calif.) and Shimadzu GC-FID analysis. The liquid phase after reaction was filtered through a 0.45 micron syringe filter before being diluted 10 times with ethanol. The sample were injected in an Agilent 6890 series GC/MS equipped with an Agilent DB5-MS column (30 m×0.25 mm ID, 0.25 μm film thickness) and an Agilent 5973 Mass Selective Detector. The same prepared samples were also injected in a Shimadzu GC-2010 equipped with an SHRXI-5MS column (30 m×0.25 mm ID, 0.25 μm film thickness) and an FID detector. C4 compounds of ethyl vinylglycolate and ethyl 2-hydroxybutanoate were estimated by ethyl 3-hydroxybutanoate standard.

The gaseous products were analysed by a Shimudzu GC-2014 gas chromatograph equipped with a HAYESEP-N column (2.5 m×⅛ in×2.1 mm, stainless steel, Hayes Separations, Inc., Bandera, Tex.), a HAYESEP-D column (2.5 m×⅛ in×2.1 mm, stainless steel), a HAYESEP-S column (2 m×⅛ in×2.1 mm), a HAYESEP-D column (1 m×⅛ in×2.1 mm), a MOL SIEVE 5A column (3 m×⅛ in×2.1 mm, stainless steel), a Carbowax column (2 m×⅛ in×2.1 mm) and a thermal conductivity detector (TCD). The gaseous products were injected with carrier gas (He) at a flow of 40 ml/min and a column temperature of 55° C. The injection volume was 1000 μl.

A Euro EA3000 CHNS-O analyzer (Eurovector) was used to measure the carbon content in the solid residue samples.

EXAMPLE 2

Production of Methyl Lactate from Carbohydrates Using Mesoporous Zr-SBA

The production of value-added chemicals from carbohydrates using non-toxic heterogeneous catalysts is an appealing environmentally benign process. One approach to overcoming mass-transfer limitations that may be associated with certain catalyst supports, such as zeolites, is to increase the diameter of the pores, thus bringing them into the mesoporous range, with a key factor being the shape selectivity properties of the catalyst. Shape selectivity enables excellent adjustment of catalytic transformation exclusivity, and also acts on the activity and stability of the catalyst by either protecting the acid sites from potential contaminants (in particular, coke precursors), which are contained in the feeds, or by inhibiting the formation of coke precursors in the pores.

Pure mesoporous silica materials typically possess a neutral framework, as well as a propensity to exhibit traits such as poor hydrothermal stability and low catalytic activity, which can limit their application. The properties of mesoporous silicate materials can be enhanced by incorporating metal ions into the host mesoporous silica material. In particular, the isomorphic substitution of silicon with transition metals can generate catalytically active sites in mesoporous silicate materials.

SBA-15 is a mesoporous material having a 2D hexagonal-ordered structure with comparatively large, tunable pores in the 4-10 nm range and high hydrothermal stability compared with other mesoporous silica materials, such as MCM-41, its analog in M41S family. The large pore channel network provides a distinctive open space, with easy and direct access for both guest and host species, thus facilitating inclusion and/or diffusion throughout the pore channels without pore blockage.

Zirconia-based materials may be useful in catalyzing various types of reactions, such as oxidation, dehydration, hydrogenation, and hydroxylation. Mesoporous silicate materials containing zirconium can have high special surface areas and potential Lewis acid properties. The basic structural unit of mesoporous silicate frameworks consists of a silicon atom that is coordinated to four oxygen atoms. Zirconium atoms have a coordination number of 7 or 8 in zirconia materials. When replacing $Si^{4+}$ with $Zr^{4+}$, a zirconium atom has only 4 coordinated oxygen atoms, resulting in empty zirconium d-orbitals, which can act as electron acceptors, i.e. Lewis acid sites.

Carbohydrates constitute the largest portion of lignocellulosic biomass, and would be useful as a commercial chemical feedstock, such as a petroleum supplement or replacement for producing value-added chemicals. The synthesis of lactate acid esters in related alcohols with renewable carbohydrate biomass as the feedstock could provide a route to "green" solvents, which could have numerous applications in the chemical, food, pharmaceutical, and cosmetic industries.

Alcohols may be used as an alternative solvent in the liquefaction of various types of biomass, including cellulose, lignin, sewage sludge, and microalgae, due to their advantages of better solubility of organic intermediates, hydrogen donor properties, and easier separation due to their low boiling points. Compared with water, alcohols, such as methanol and ethanol, can have much lower critical temperatures and pressures. Thus at relatively mild conditions, near-critical and supercritical alcohols can act not only as a solvent, but also as a reactant which can serve as a hydrogen donor agent to remove oxygen from biomass and a radical quenching agent to retard repolymerization and formation of humins. Methanol, a small and highly polar molecule, still exhibits weak hydrogen bonding even at the critical temperature (Tc=239.4° C.), which facilitates the methanolysis of large biomass molecules.

This Example describes the catalytic conversion of carbohydrates to methyl lactate using a mesoporous Zr-SBA-15 catalyst in near-critical methanol solvents (T<240° C.), which combines lactic acid production and esterification in a "one-pot" reaction system. Without limiting the scope of the present disclosure, a possible reaction mechanism and structure-activity relationship are proposed to explain the performance of the Zr-SBA-15 as a heterogeneous Lewis acid catalyst in the production of ML from various carbohydrates, including pentose, hexose, starch and cellulose.

Materials

The following reagents and products were used as received without further purification. D-(+)-xylose (99%), D-(+)-glyceraldehyde (98%), Fructose (99%), Sucrose (99%), glycolaldehyde dimer, pyruvaldehyde (40 wt % solution in water), furfural (99%), 5-(hydroxymethyl) furfural (99%), hydrochloric acid (36.5-38.0%, BioReagent), triblock copolymer Pluronic P123, tetraethyl orthosilicate (>99.0%), n-butanol (>99.0%), and zirconyl chloride octahydrate (98%) were purchased from Sigma Aldrich (St. Louis, Mo.). D(+)-Glucose (Reagent ACS Grade) was purchased from Acros Organics (Morris Plains, N.J.). Methyl lactate (97%), erythrose syrup (70% w/v), methyl levulinate (99%), methyl glycolate (98%), and glycolaldehyde dimethylacetal (98%) were purchased from Alfa Aesar (Ward Hill, Mass.). Microcrystalline cellulose (average particle size 50 μm) and cellobiose (98%) were purchased from Acros Organics (Morris Plains, N.J.). Starch (powder, certified ACS, soluble) and sucrose (crystalline, certified ACS) were purchased from Fisher Scientific (Pittsburgh, Pa.). Galactose, mannose, and arabinose were purchased from Carbosynth (Compton, Berkshire UK).

Catalyst Preparation

The Zr-SBA-15 materials were synthesized following the procedure described by Chen, et al., "Synthesis of Zr-incorporated SBA-15 Mesoporous Materials in a Self-Generated Acidic Environment," *Chem. Mater.* 16 (2004) 4174-4180, incorporated by reference herein to the extent not inconsistent with the present disclosure. Briefly, 2 g of Pluronic P123 was added to 75 ml of 1.6 M HCl solution. The mixture was stirred at 40° C. for 3 hours until all P123 was dissolved. Next, 4.25 g of TEOS and an appropriate amount of zirconyl chloride octahydrate were added into the solution and the mixture was stirred for another 24 hours at 40° C. The resulting gel was placed in a Teflon-lined autoclave and heated at a range of temperatures of 80-150° C. for 24 hours. The solid product was filtered with mild washing, dried at 100° C. overnight, and calcined in flowing air at 550° C. for 6 hours. In Zr-SBA-15-x-y ° C., x represents the mole ratio of Si/Zr, while y represents the hydrothermal temperature. Zr-SBA-15-y ° C. without x means that the molar ratio of Si/Zr was 20. Zr-SBA-15-x without y means that the catalyst was synthesized at 100° C. Zr-SBA-15 without x and y means that the catalyst was synthesized at 100° C. with Si/Zr=20.

Catalyst Characterization

Small-angle X-ray Scattering (SAXS) was performed using a sample-to-detector distance of 172.1 cm, which provided a two-theta range of approximately 0.3-2.0 degrees. Data was typically collected over 30 seconds at a temperature of 20° C. The X-ray source was Cu Kα radiation with a wavelength of 1.54 Å, which was generated by a Rigaku Ru-200BVH rotating anode. Measurements were made on a Siemens HI-STAR multi-wire area detector (Siemens Analytical X-ray Instruments, Madison, Wis.) and were corrected for background and non-linearities in the detector. Integration of the 2D measurement provided a 1D plot of intensity (arbitrary units) versus the two-theta scattering angle, which was peak-fitted using Material Data Incorporated's JADE.

Transmission electron microscope (TEM) micrographs were captured using a JEOL-JEM 2100F (JEOL USA, Inc., of Peabody, Mass.) operating at 200 kV. The samples were dispersed in 1-butanol, and a drop of the suspension was placed on lacey carbon supported on 300 mesh copper grids.

$N_2$ physisorption isotherms were measured on an Autosorb-iQ system (Quantachrome Instruments of Boynton Beach, Fla.) at 77 K. Outgassing was carried out at 523 K until pressure rise in the test cell was less than 25 mTorr/min. Pore size distribution and cumulative adsorbed volume were calculated by using the NLDFT (nonlocal density functional theory) adsorption model which describes $N_2$ adsorbed onto silica at 77 K in cylindrical pores (AsiQwin 1.02, Quantachrome). The NLDFT model considers the configuration of adsorbates in pores on a molecular level and is widely used to characterize ordered porous materials with different pore geometries. With adequate fluid-fluid and fluid-solid interaction parameters, it has been used to quantitatively predict the capillary condensation and evaporation transitions of adsorbates in mesoporous materials.

In a typical $NH_3$ temperature programmed desorption (TPD) experiment using a Micromeritics AutoChem II 2920 Chemisorption Analyzer (Micrometrics Instrument Corp., of Norcross, Ga.), the catalyst was first degassed in helium at 250° C. for 1 hour, then the temperature was cooled to 100° C. in helium flow. After that, 10% ammonia in helium was adsorbed on the catalyst at 100° C. for 60 minutes and then helium flowing at 50 mL/min was used to remove physically adsorbed ammonia. Finally, $NH_3$ TPD was carried out from 100° C. to 550° C. with a temperature ramp of 10° C./min.

A drift-IR study was performed on an EQUINOX 55 (Bruker Optics Inc., of Billerica, Mass.) equipped with a MCT detector. The samples were degassed at 550° C. for 1 hour under helium in a high temperature reaction chamber containing a Praying Mantis™ diffuse reflection attachment (Harrick Scientific Products, Inc., of Pleasantville, N.Y.). Small aliquots of pyridine were carried by helium and exposed to the sample at room temperature for 15 minutes. Prior to the characterization, the physically-adsorbed pyridine was removed by flowing helium at 250° C. under helium for 1 hour. All spectra were collected at 120° C.

Catalytic Reactions

Reactions were carried out in a 100 mL stirred Parr micro reactor, whereby the catalyst was suspended in a solution of biomass substrate in methanol (20 ml) and the reactor was charged with 400 Psi $N_2$ initially and then heated at a ramp rate of 10° C./min until the desired set temperature was reached. During the reaction, mixing was achieved through an internal propeller operating at 700 RPM. Once the set temperature was attained, the reactor was held for the set reaction time, and then quenched quickly in an ice bath to stop the reaction. The reactor was cooled to approximately 25° C. before being vented after the gas pressure was recorded. The reactor was then immediately broken down and the solid residue remaining in the reactor was recovered and dried. The aqueous and solid fractions were separated using a centrifuge.

Product Analysis

After reaction, the resultant liquid phase product samples were prepared for analysis with a gas chromatograph coupled with a flame ionization detector (GC-FID), a high performance liquid chromatography (HPLC), and a gas chromatograph coupled with a mass spectrometer (GC-MS).

The liquid products (e.g. furfural, HMF) were quantified by HPLC analysis using a Shimadzu HPLC system (Kyoto, JP) equipped a UV-VIS Detector (Shimadzu SPD 10-AV) and Refractive Index Detector (Shimadzu RID-6A). The liquid phase after reaction was filtered through a 0.45 micron syringe filter, and then diluted 10 times with DI water. The samples were separated in an Aminex 87-H column from Bio-Rad (Hercules, Calif.), using 5 mM $H_2SO_4$ as the mobile phase (0.7 mL/min flow rate) at a column temperature of 55° C. The UV-VIS detector was operated at 208 nm and 290 nm.

The liquid products identified in the methanol were qualified and quantified by GC-MS and GC-FID analysis, respectively. The liquid phase after reaction was filtered through a 0.45 micron syringe filter before being diluted 10 times with methanol. The samples were injected in an Agilent 6890 series GC-MS (Agilent Technologies, Inc., Santa Clara, Calif.) equipped with an Agilent DB5-MS column (30 m×0.25 mm ID, 0.25 μm film thickness) and an Agilent 5973 Mass Selective Detector. The same prepared samples were also injected in a Shimadzu GC-2010 equipped with an SHRXI-5MS column (30 m×0.25 mm ID, 0.25 μm film thickness) and a FID detector.

The gaseous products were analysed by a Shimadzu GC-2014 gas chromatograph equipped with a SH-Rtx-Wax capillary column (30 m×0.32 mm×1 μm); a HAYESEP-N column (2.5 m×⅛ in×2.1 mm, stainless, Hayes Separations, Inc., Bandera, Tex.), a HAYESEP-D column (2.5 m×⅛ in×2.1 mm, stainless), a HAYESEP-S column (2 m×⅛ in×2.1 mm, stainless), a HAYESEP-D column (1 m×⅛ in×2.1 mm, stainless), a MOL SIEVE 5A column (3 m×⅛ in×2.1 mm, stainless) and a thermal conductivity detector (TCD). The gaseous products were injected with carrier gas (He) at a flow rate of 40 ml/min at a column temperature of 55° C. The injection volume was 1000 μl.

Results and Discussion

Figure 19:
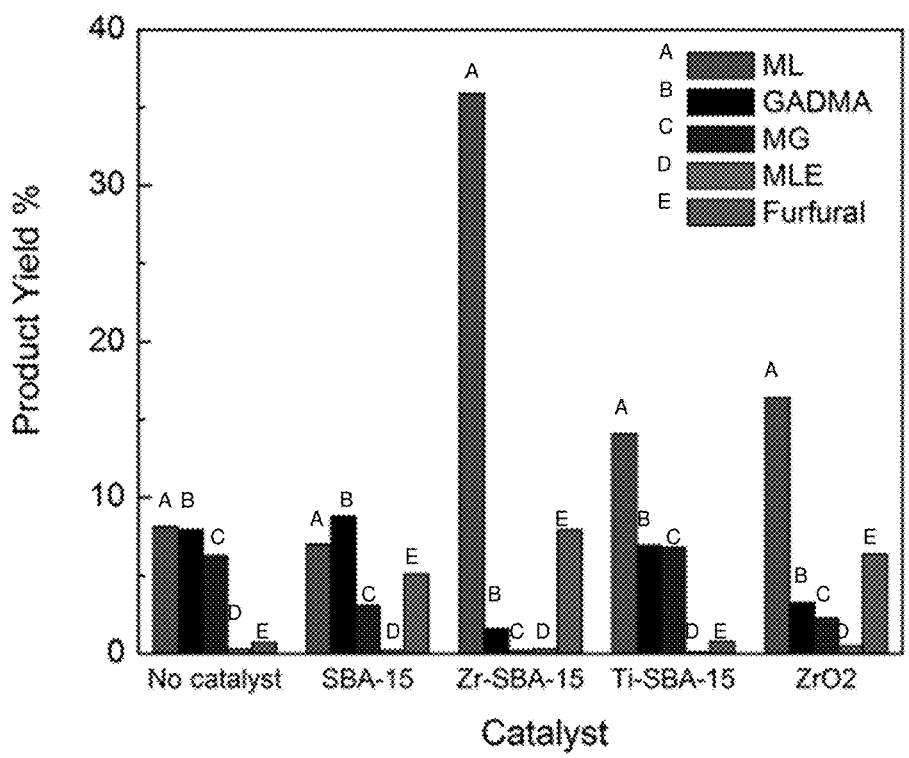
FIG. 19 is a graph of product yields (%) obtained from the conversion of xylose (0.2 g) in methanol using 0.1 g of various catalysts for 1 hour at 240° C. and an initial $N_2$ pressure of 400 psi.

FIG. 19 shows the yields of the main products (ML: Methyl lactate, GADMA: Glycolaldehyde dimethyl acetal, MG: Methyl glycolate, MLE: Methyl levulinate) using xylose as the feedstock with and without adding catalysts. A relatively low yield of methyl lactate (ML) (~8%) was produced at 240° C. without adding a catalyst. With only pure SBA-15, the ML yield was ~7.0%, which is close to that without catalyst. Both the as-synthesized Zr-SBA-15 and the commercial $ZrO_2$ resulted in noticeably higher yields of ML at 240° C. for 1 hour. The 35.9% yield of ML was achieved with the Zr-SBA-15 catalyst, which was more than twice the 16.4% yield obtained with the $ZrO_2$ catalyst.

To validate the catalytic effect of Zr ions in SBA-15, Ti ions were deliberately incorporated into the SBA-15 framework so as to compare with the Zr-SBA-15 catalyst. It was found that with the Ti-SBA-15 catalyst, the yield of ML from xylose was comparable to that with the $ZrO_2$ catalyst but was still much lower than that with the Zr-SBA-15 catalyst. Notably, without a catalyst or with the Ti-SBA-15 catalyst, there were negligible amounts of furfural produced, 0.7% and 0.8%, respectively. In contrast, when SBA-15, $ZrO_2$, and Zr-SBA-15 were employed, the furfural yields reached 5.1%, 6.4% and 7.9%, respectively.

The mesoporous structure of the silica framework with the presence of zirconium ions confers strong Lewis acidity as well as weak Brønsted acidity. Lewis acid catalysis can facilitate the retro-aldol condensation of a sugar molecule, which is the initial step in the conversion of sugars to lactic acid, while a Brønsted acid catalyzes the dehydration of xylose to form furfural. The co-production of ML and furfural from xylose with the Zr-SBA-15 catalyst suggests that both the Lewis and Brønsted acidic properties co-exist on the catalyst surface.

Figure 20:
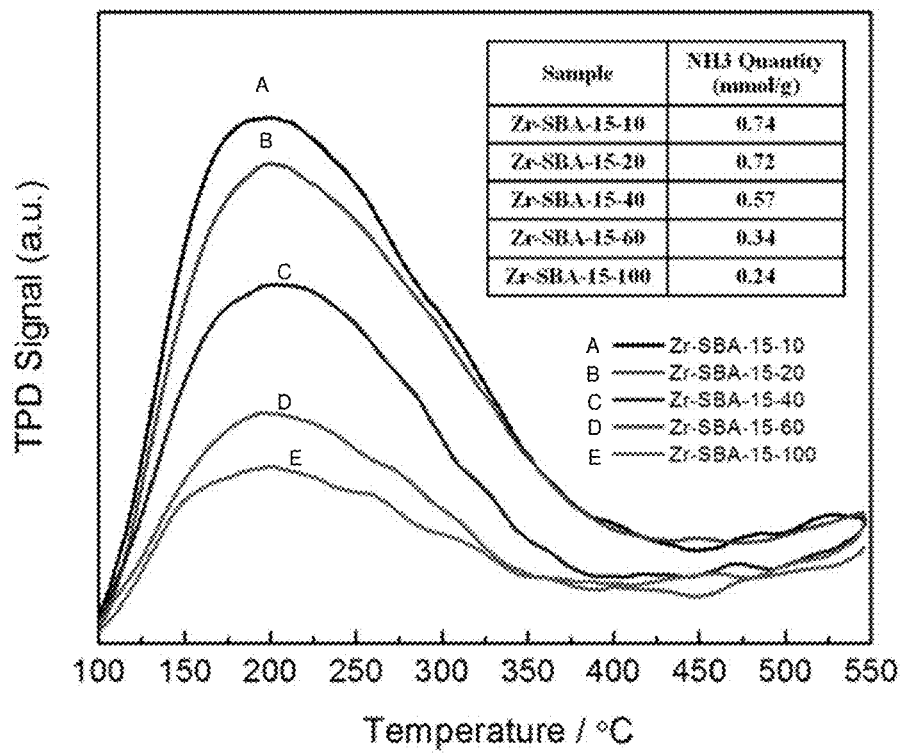
FIG. 20 is a graph of temperature-programmed desorption signal (arbitrary units) versus temperature (° C.) for the temperature-programmed desorption of ammonia ($NH_3$-TPD) for Zr-SBA-15 materials synthesized at a hydrothermal temperature of 100° C. with different Si/Zr molar ratios.
Figure 21:
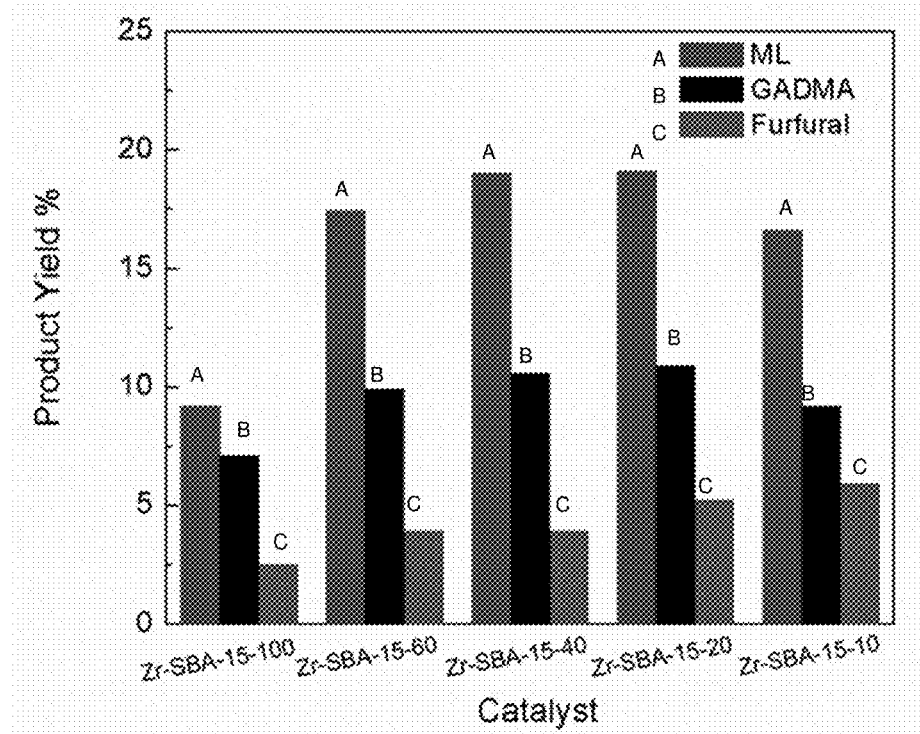
FIG. 21 is a graph of product yield (%) for the conversion of xylose in methanol versus SBA-15 catalysts with different Si/Zr molar ratios.

To further examine the catalytic effect of zirconium loading of the Zr-SBA-15 catalyst, the catalysts with different Si/Zr molar ratios of 100:1, 60:1, 40:1, 20:1 and 10:1 were prepared. As shown in FIG. 20, the total acid strength analysed by the NH₃ TPD increased with increasing the zirconium loading on the SBA-15 silicate. FIG. 21 shows the yields of the three major products, ML, glycoladehyde dimethyl acetal (GADMA), and furfural, over the Zr-SBA-15 catalysts with various Si/Zr molar ratios under otherwise identical reaction conditions (60 minutes at 180° C. and an initial $N_2$ pressure of 400 psi using 0.2 g xylose and 0.1 g catalyst). Initially, with increasing Zr loadings, the yields of the three major products steadily increased. However, as the zirconia loading further increased to a Si/Zr mole ratio of 10:1, the yields of all three products decreased, implying an abrupt change in the catalyst properties. The maximum yield of ML was found to be in the range of the Si/Zr mole ratios of 40:1 to 20:1, e.g., with the Zr-SBA-15-40 or Zr-SBA-15-20 catalyst, approximately 19% ML and 11% GADMA were produced at 180° C. However over-loading Zr ions onto SBA-15 inhibited the catalyst's performance.

Figure 22:
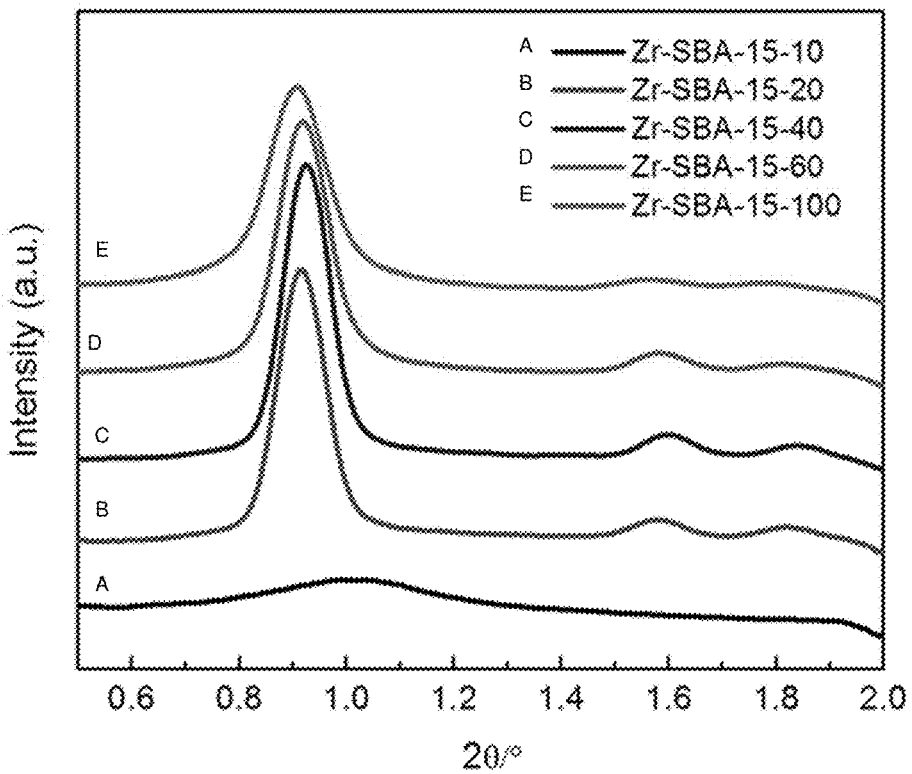
FIG. 22 presents the small-angle X-ray scattering patterns of Zr-SBA-15 materials synthesized at a hydrothermal temperature of 100° C. with different Si/Zr molar ratios.
Figure 23:
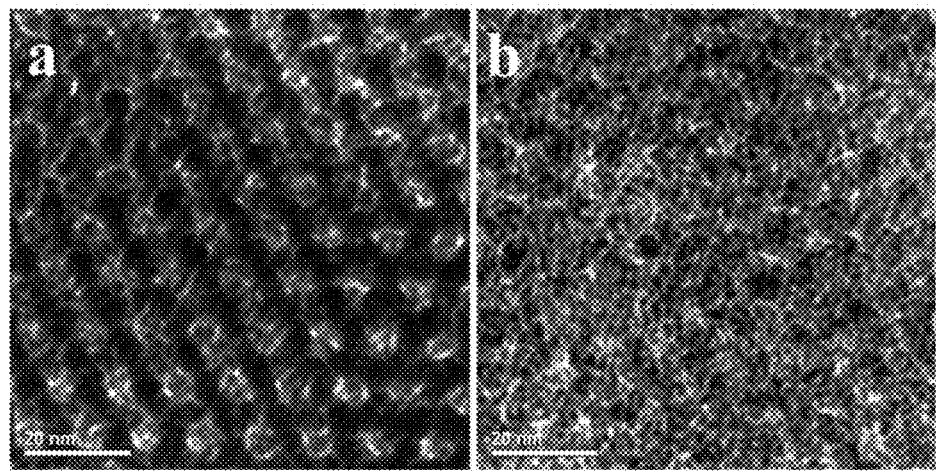
FIG. 23 is high-resolution transmission electron microscopy (HRTEM) images of (a) Zr-SBA-15 at a Si/Zr ratio of 20 and (b) Zr-SBA-15 at a Si/Zr ratio of 10.

To confirm the structures of the Zr-SBA-15 silicate materials at different Si/Zr ratios, small-angle X-ray scattering (SAXS) characterization was performed. As depicted in FIG. 22, the SAXS spectra exhibited strong (1 0 0), (1 1 0), and (2 0 0) diffraction peaks at 2θ angles between 0.5° and 2° for the samples with the Si/Zr ratios from 100:1 to 20:1, which indicated the structural ordering with the symmetry of the 2D-hexagonal space group p6 mm. However, a further increase in Zr loading (Si/Zr=10:1) drastically lowered the peak intensity, suggesting that incorporating too many Zr heteroatoms was detrimental to the structure of the mesoporous SBA-15 framework, which was coincident with its low catalytic performance. From high-resolution TEM images (FIG. 23), a highly ordered pore structure was evident for the Zr-SBA-15 materials at the Si/Zr mole ratio of 20:1, while the ordered mesoporous structure was destroyed when the Si/Zr mole ratio reached 10:1, consistent with the SAXS data.

Figure 24:
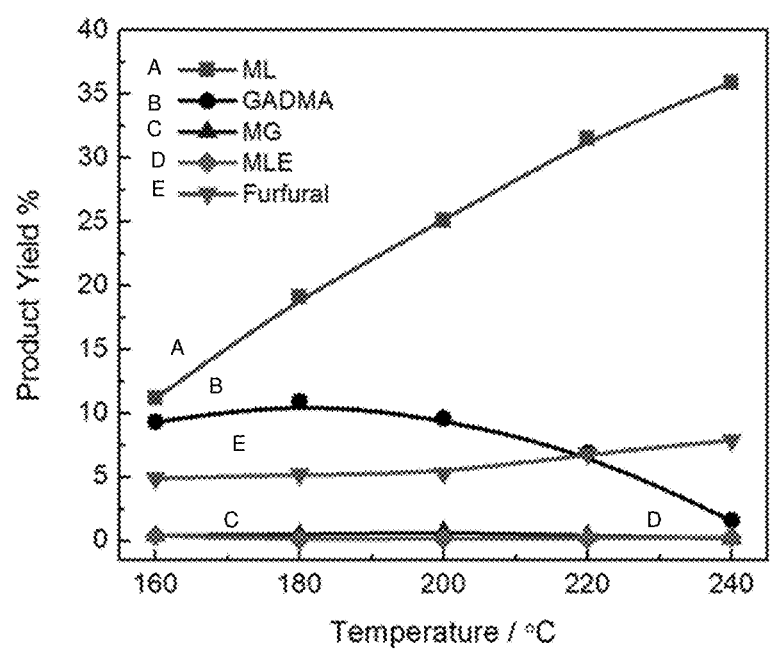
FIG. 24 is a graph of liquid-phase product yield (%) versus reaction temperature (° C.) from conversion of 0.2 g xylose with 0.1 g of Zr-SBA-15 catalyst in methanol using reaction conditions of 1 hour, 400 psi initial $N_2$ pressure, and 0.2 g xylose.

To maximize ML yield, process conditions were optimized for the xylose conversion reactions. As shown in FIG. 24, varying the temperature has a pronounced effect on the production of ML, yielding a steadily increasing amount of ML up to 35.9% with an increase in temperature from 160° C. to 240° C. for a 1-hour reaction. The yields of other products, such as furfural, also increased steadily with increasing temperature.

Figure 25:
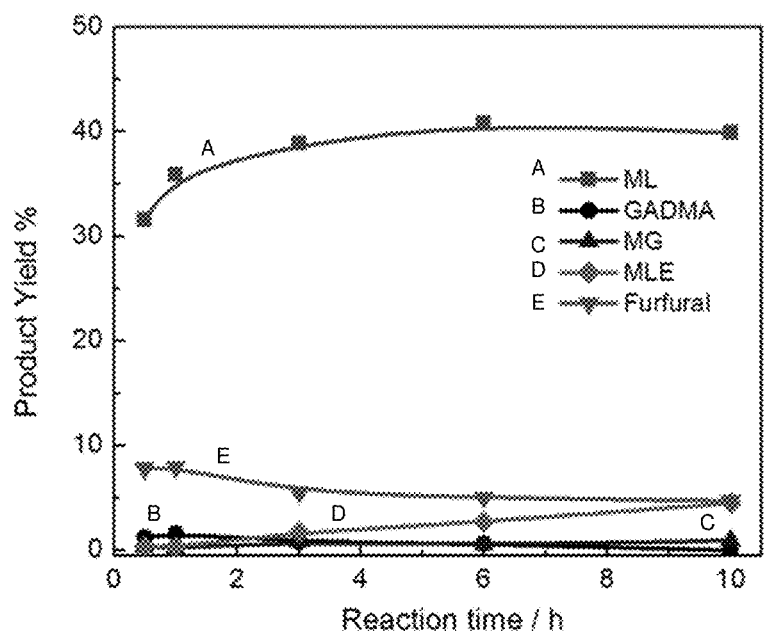
FIG. 25 is a graph of liquid-phase product yield (%) versus reaction time (hours) for the conversion of 0.2 g xylose with 0.1 g Zr-SBA-15 catalyst in methanol at 240° C. and an initial $N_2$ pressure of 400 psi.

The yield of GADMA, however, decreased from 10.9% at 180° C. to 1.6% at 240° C. The highest ML yield of 40.8% was achieved when the reaction time was extended to 6 hours at 240° C., as shown in FIG. 25. However, the ML yield varied little with reaction times longer than 3 hours. The yields of GADMA and furfural consistently decreased with extended reaction times. GADMA almost completely vanished after 3 hours at 240° C. These results suggest that longer reaction times leads to the decomposition of GADMA and furfural. The methyl levulinate yield increased with reaction time at 240° C.

Figure 26:
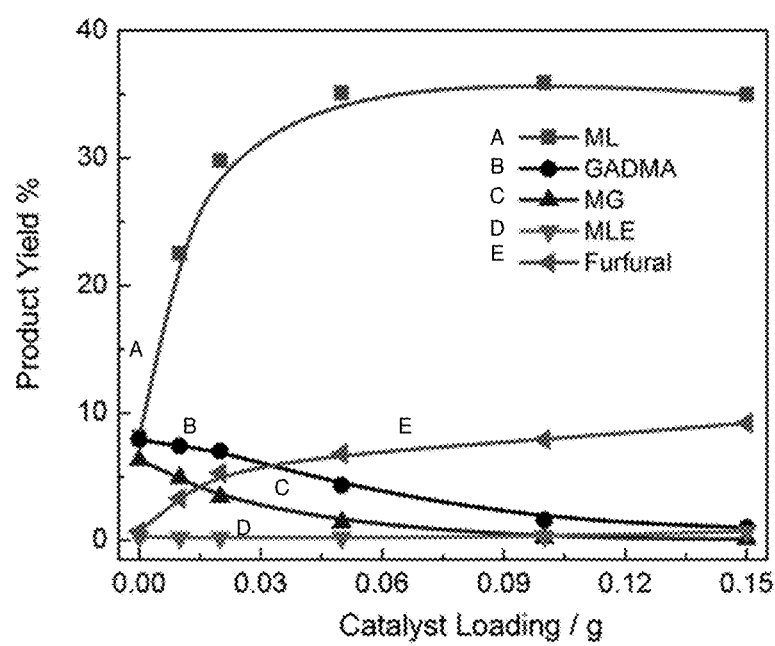
FIG. 26 is a graph of liquid-phase product yield (%) versus catalyst loading (g) for conversion of 0.2 g xylose with Zr-SBA-15 catalyst in methanol at 240° C. for 1 hour at an initial $N_2$ pressure of 400 psi.

The effects of different catalyst loading amounts on the conversion of xylose were also examined. As depicted in FIG. 26, the yields of both ML and furfural showed a similar uptrend with increasing catalyst loadings, while those of GADMA and methyl glycolate decreased steadily. However, when the mass ratio of catalyst to xylose was larger than 0.2, the yield of ML was almost unchanged and plateaued. By substituting methanol with water as the solvent (FIG. 27 entry 4), the lactic acid yield was ~5.9%, while the furfural yield was ~42.3% with Zr-SBA-15. In contrast, the yields of furfural and lactic acid were only 21.2% and 3.0%, respectively, without adding any catalyst. Thus the Lewis acid property of the Zr-SBA-15 catalyst appeared to vanish and be transformed to a Bronsted acid in water.

Figure 28:
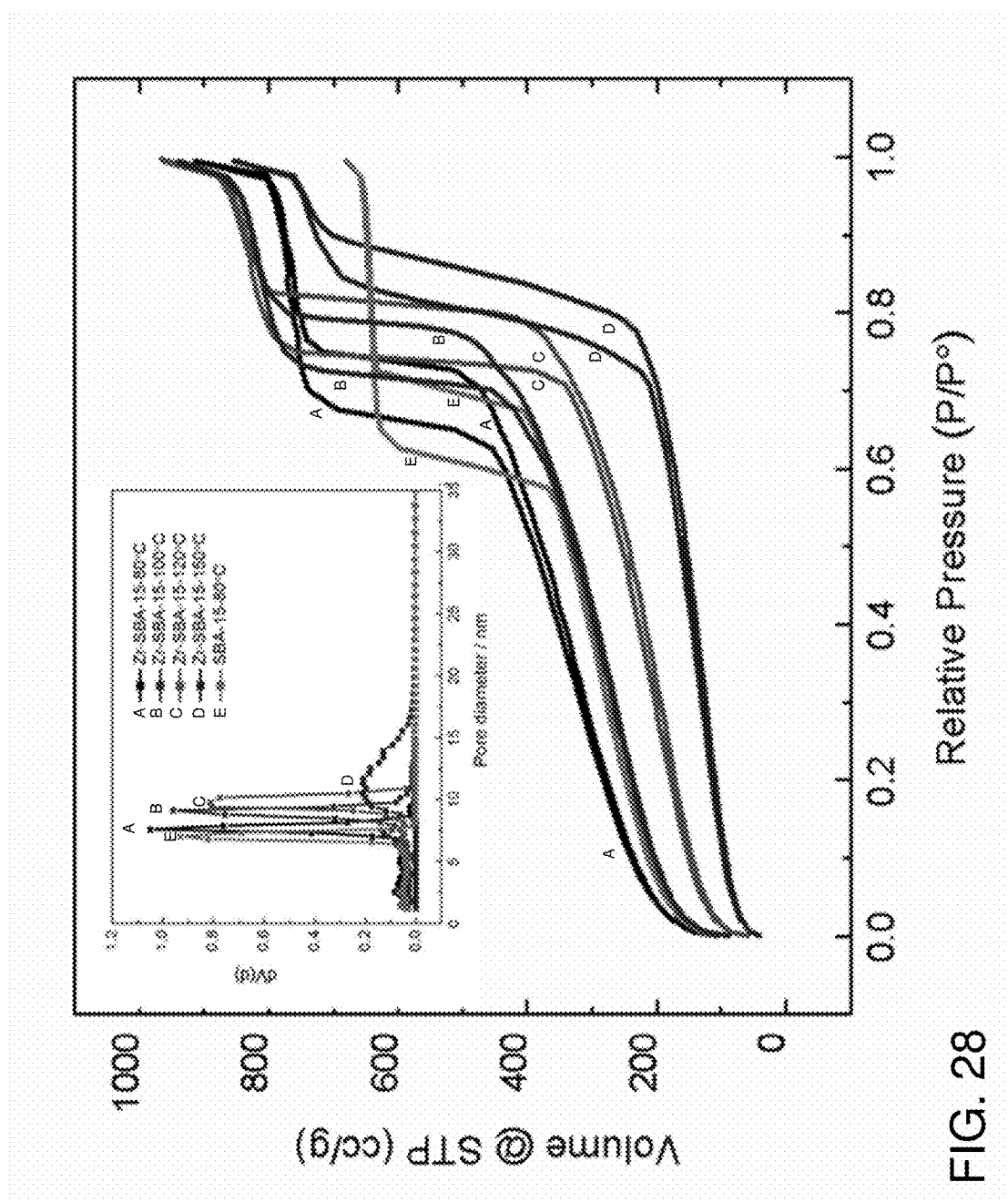
FIG. 28 is a graph of volume (cc/g) versus relative pressure (pressure/initial pressure) for nitrogen adsorption-desorption isotherms of Zr-SBA-15 materials, with an inset illustrating the pore size distribution determined by a NLDFT model for adsorption of $N_2$ on silica at 77K (cylindrical pore model).

For chemical reactions in confined channel spaces in mesoporous silicate materials, the pore size may affect catalyst properties. The pore size of the Zr-SBA-15 catalyst can be tuned by optimizing the hydrothermal treatment conditions during synthesis. FIG. 28 shows the pore size distribution determined by the NLDFT model for Zr-SBA-15 materials with different synthesis temperatures. The pore sizes of Zr-SBA-15-80° C., Zr-SBA-15-100° C., Zr-SBA-15-120° C., and Zr-SBA-15-150° C., were 7.6, 9.1, 9.8, and 10.6 nm, respectively. As illustrated in FIG. 30, with increasing hydrothermal temperatures, the pore diameter of the SBA-15 materials increased, while the BET surface area decreased.

The ML yield varied slightly with increasing pore size, except the catalyst synthesized at 80° C. with the smallest pore size, as shown in FIG. 29. In contrast, the furfural yield and the corresponding solid residue yield decreased significantly with increasing pore size. Aldehyde compounds, such as furfural, are prone to polymerize and form humins at elevated temperatures. Apparently, large pores in a Zr-SBA-15 catalyst provide more open pore space, where guest and host species can easily interact, thus facilitating diffusion in and out of the stoma channels without pore restriction. To minimize undesirable by-products such as furfural and humins, it may be beneficial to lift the pore diffusion limit of the Zr-SBA-15 catalyst for this particular ML production reaction.

Figure 32:
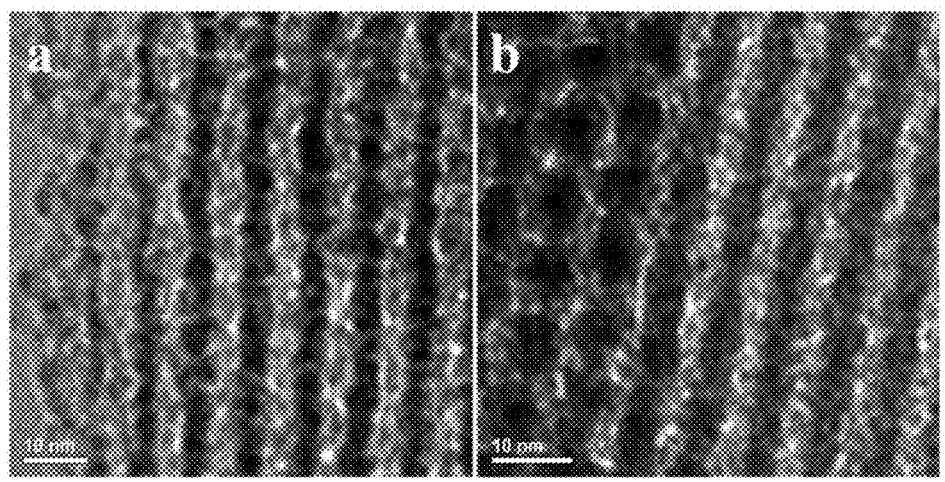
FIG. 32 is high-resolution transmission electron microscopy (HRTEM) images of (a) fresh Zr-SBA-15; and (b) spent Zr-SBA-15 after five consecutive runs.

Recyclability and reusability are of importance for heterogeneous Zr-SBA-15 catalysts. During a typical reaction, the yield of solid residue on the catalyst was relatively low, ~10.8%. However, the activity of the catalyst may decrease if solid residue continues to build up on the catalyst surface in subsequent reactions. FIG. 31 shows that the yield of ML from xylose only decreased slightly over five consecutive runs with the re-used, unregenerated catalyst, suggesting that the Zr-SBA-15 catalyst was relatively stable. However, it still may be beneficial to periodically apply a regeneration process to remove any solid residue. The yield of solid residue (10.7%) on the catalyst after the 5$^{th}$ run almost did not change compared with that after the first run (10.8%), implying that the formation of extra coke inside the pores was inhibited after the catalyst was used once. High-resolution TEM images, FIG. 32, of the Zr-SBA-15 samples before and after reaction showed that the highly ordered pore structure was maintained without any noticeable pore size shrinkage or blockage.

Figure 33:
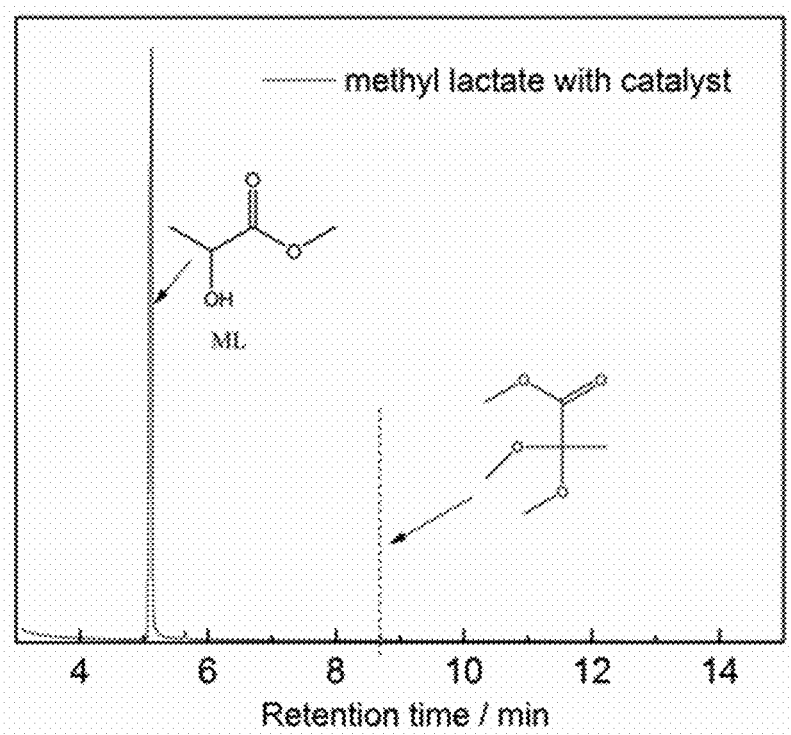
FIG. 33 is the GC/MS spectra of a sample in methanol from the interaction of 0.2 g methyl lactate with 0.1 g Zr-SBA-15 catalyst in methanol for 1 hour at 240° C. and an initial $N_2$ pressure of 400 psi.

To evaluate the stability of ML over the Zr-SBA-15 catalyst, ML was used as a reactant. It was found that only 3% of ML decomposed after a one-hour reaction at 240° C. with the Zr-SBA-15 catalyst in methanol (FIG. 33), indicating that ML, the final product of xylose conversion, was very stable in this reaction system.

Figure 34:
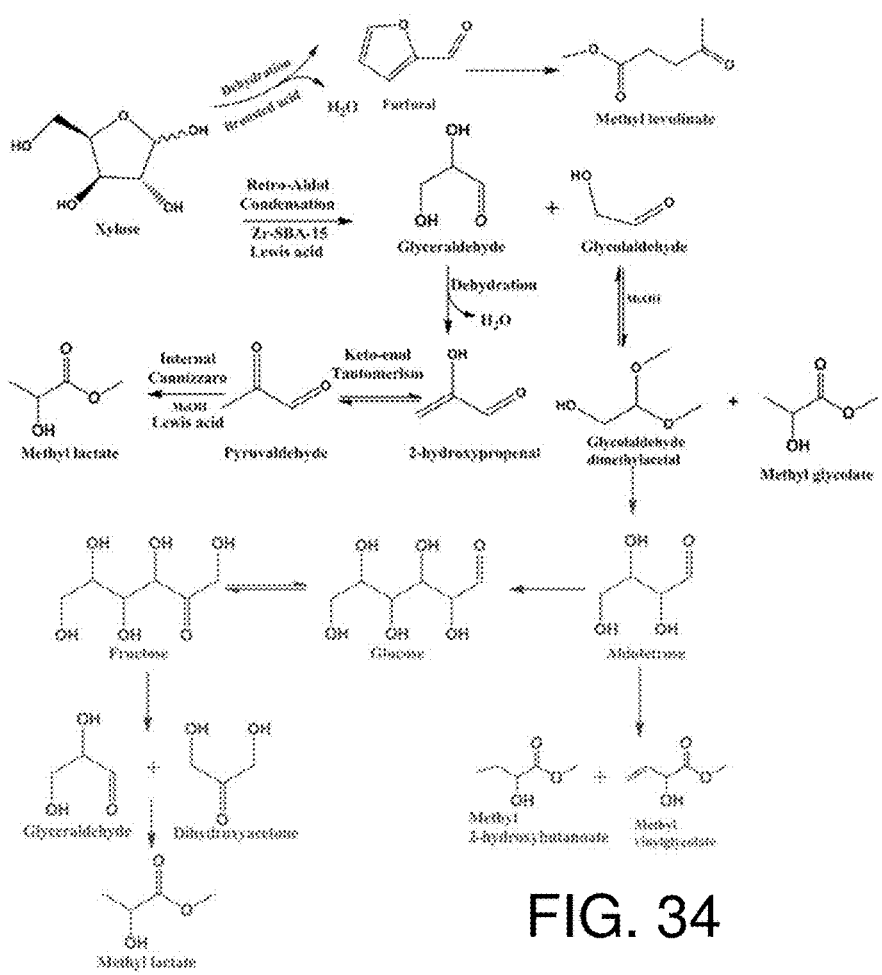
FIG. 34 illustrates a proposed reaction mechanism for the conversion of xylose to methyl lactate and other intermediate and final products in methanol solvent with Zr-SBA-15 catalyst.
Figure 35:
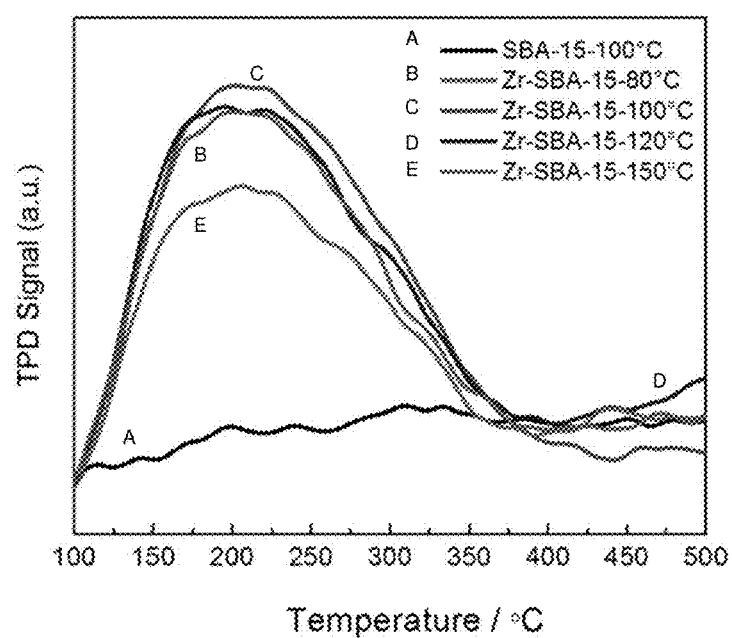
FIG. 35 is a graph of temperature-programmed desorption signal (arbitrary units) versus temperature (° C.) for the temperature-programmed desorption of ammonia ($NH_3$-TPD) for Zr-SBA-15 materials synthesized at different hydrothermal temperatures and a Si/Zr ratio of 20.

Lewis acids can promote retro-aldol condensation as the initial step in the conversion of sugars to lactic acid. The reaction pathway of converting xylose to ML over the Zr-SBA-15 catalyst may begin at the retro-aldol condensation, forming glycolaldehyde and glyceraldehyde, as shown in FIG. 34. FIG. 35 illustrates the total acidity of the Zr-SBA-15 samples calculated from the NH₃ TPD. The pure SBA-15 silicate did not show any appreciable ammonia adsorption (only 0.02 mmol NH₃/g), while the Zr-SBA-15 samples presented high acidity of ~0.7 mmol NH₃/g. Pyridine-FTIR demonstrated that Lewis acid sites were dominant on the Zr-SBA-15 catalyst.

The $Zr^{4+}$ ions in the SBA-15 silica framework, as the Lewis acid sites, first interacted with the carbonyl group of xylose, and then broke the C5 xylose molecule down to C3 glyceraldehyde and C2 glycolaldehyde. Glyceraldehyde underwent dehydration to form 2-hydroxypropenal, then to pyruvaldehyde via keto-enol tautomerization, and finally to ML in methanol solvent by possible intramolecular Cannizzaro and esterification reactions. Although trioses were able to be converted to ML via Meerwein-Ponndorf-Verley reduction with methanol, the direct evidence of converting pyruvaldehyde to ML through intramolecular Cannizzaro reaction was that no deuterium was incorporated into the hydrocarbon backbone of ML in the isotopic $CD_3OD$ solvent. On the other hand, the by-product, GADMA, was formed by the acetalization of glycolaldehyde with methanol.

To validate this reaction pathway, the possible key intermediates, glyceraldehyde, dihydroxyacetone, pyruvaldehyde, glycolaldehyde, and GADMA were used as probe reactants. It was found that much higher ML yields (78.8% and 84.5%) were obtained from glyceraldehyde and dihydroxyacetone, respectively (FIG. 27, entries 5 and 7), than from xylose (FIG. 27, entry 13). The yield of ML was close to 100% from pyruvaldehyde (FIG. 27, entry 9). However, in the absence of the Zr-SBA-15 catalyst, much lower amounts of ML were produced from all three probe reactants.

Figure 36:
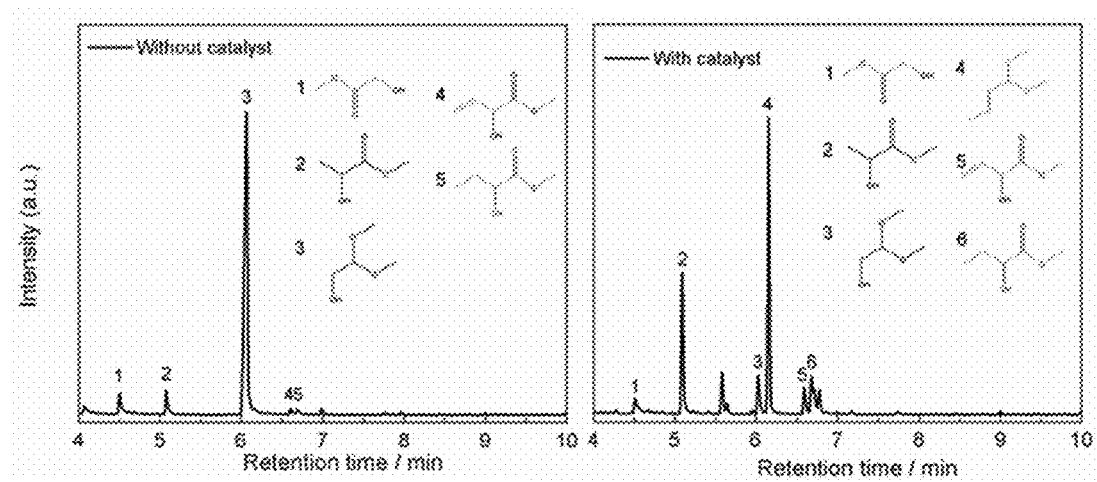
FIG. 36 is the GC/MS spectra of the products of reacting 0.2 g glycoaldehyde in methanol solvent for 1 hour at 240° C. with and without 0.1 g Zr-SBA-15 catalyst at an initial $N_2$ pressure of 400 psi.
Figure 37:
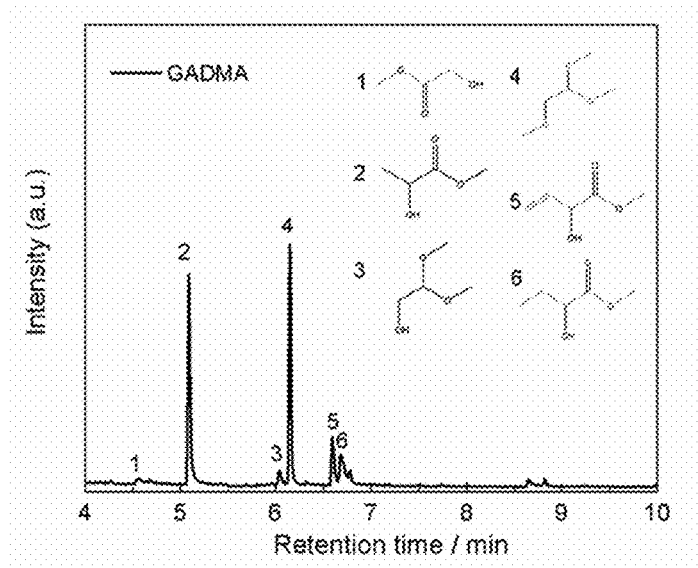
FIG. 37 is the GC/MS spectra of the products of reacting 0.2 g glycolaldehyde dimethyl acetal (GADMA) in methanol solvent with 0.1 g Zr-SBA-15 catalyst for 1 hour at 240° C. and an initial $N_2$ pressure of 400 psi.

Using glycolaldehyde as the probe, a high amount of GADMA was produced without catalyst, while ~61.3% ML was obtained with the Zr-SBA-15 catalyst. It appeared that C—C bond forming aldol condensation reactions occurred in the presence of Zr-SBA-15, in that the C4 acid ester products, e.g., methyl vinylglycolate and methyl 2-hydroxybutanoate, were also observed as the products from the C2 reactant, glycolaldehyde (FIG. 36). When using GADMA as a probe reactant, it was converted to ML in a 24% yield with the Zr-SBA-15 catalyst, and the product distribution was similar to that using glycolaldehyde as the reactant. Methoxyacetaldehyde dimethylacetal was another major product obtained through etherification while other products in much lower yields were methyl vinylglycolate and methyl 2-hydroxybutanoate, as shown in FIG. 37. GADMA and glycoaldehyde were reversibly converted to each other, and aldol-condensation reactions occurred in the presence of Zr-SBA-15 to form C4 and C6 aldehydes, while the formation of ML suggested that retro-aldol condensation reactions took place subsequently.

Figure 38:
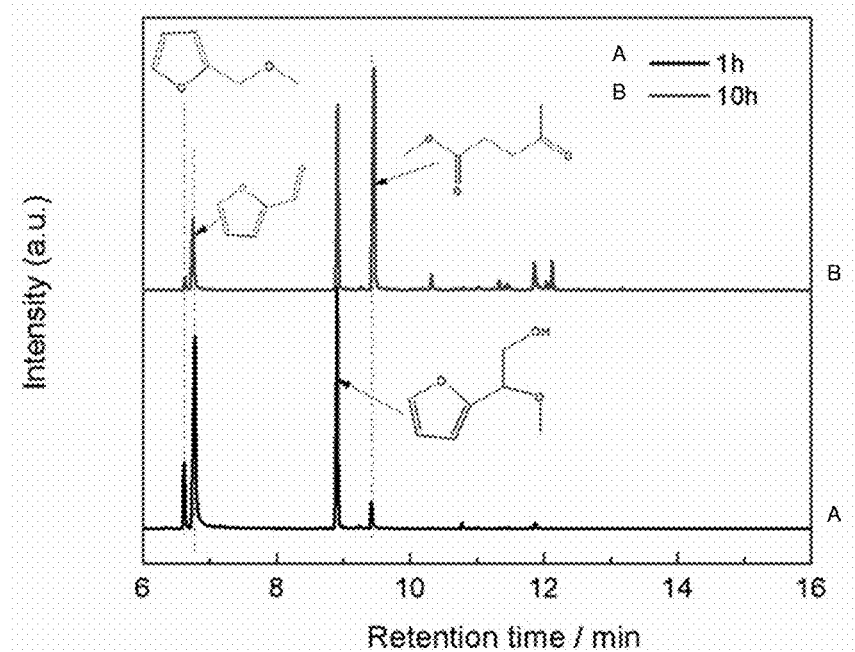
FIG. 38 is the GC/MS spectra of the products of reacting 0.2 g furfural in methanol solvent with 0.1 g Zr-SBA-15 catalyst at 240° C. at an initial $N_2$ pressure of 400 psi.

Furfural was an undesirable by-product from the dehydration of xylose, usually catalyzed by Brønsted acid sites. The furfural yield decreased sharply at high temperatures or long reaction times, while methyl levulinate yield increased at the same time during the xylose conversion with the Zr-SBA-15 catalyst. Using furfural as the probe reactant, the main product was methyl levulinate in yields of 3.6% and 33.2% after reaction for 1 hour and 10 hours, respectively, at 240° C., as shown in FIG. 38. A hydrogenation step is needed in the conversion of furfural to methyl levulinate, while methanol was the only hydrogen source in the probe reaction. Furfural may be converted into furfuryl alcohol via Meerwein-Ponndorf-Verley (MPV) transfer hydrogenation with methanol as the hydrogen donor, which is likely promoted by the Lewis acid, followed by the conversion of furfuryl alcohol into methyl levulinate through ring-opening reactions with the aid of the weak Brønsted acid sites on the Zr-SBA-15 catalyst.

The proposed reaction pathway for the conversion of xylose to ML can be generalized for the conversion of other cellulosic biomass. The retro-aldol condensation of pentoses and hexoses, however, may form different aldehyde or ketone products with solid Lewis acid catalysts. The conversion of pentoses to ML can be occur via the following steps: retro-aldol condensation of an aldopentose leads to glyceraldehyde and glycolaldehyde, while retro-aldol condensation of a ketopentose forms dihydroxyacetone and glycolaldehyde. The outcome of both reaction pathways is the formation of a triose and a glycolaldehyde.

Figure 39:
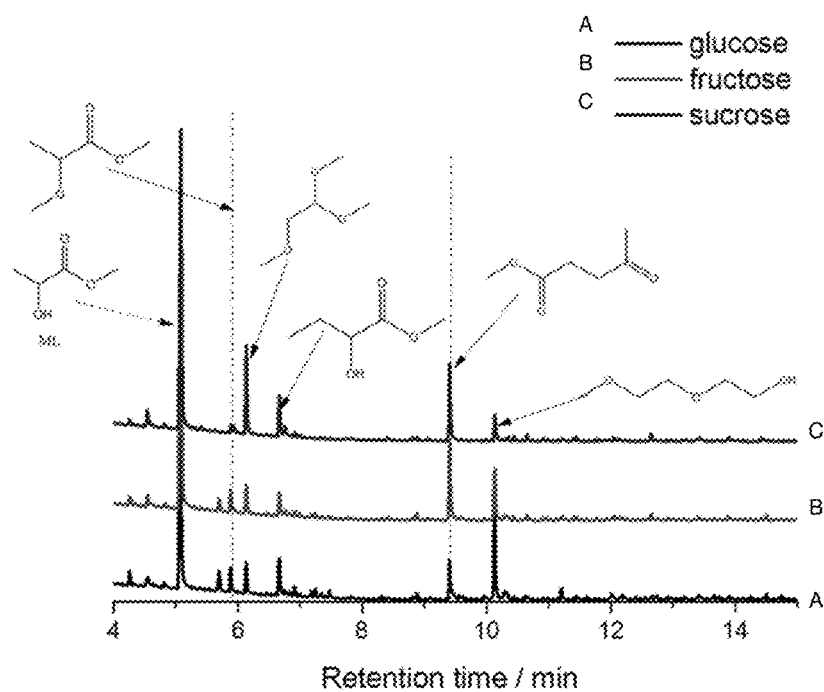
FIG. 39 is the GC/MS spectra of the products, respectively, of reacting 0.2 g of glucose, fructose, or sucrose in methanol with 0.1 g Zr-SBA-15 catalyst for 6 hours at 240° C. and an initial $N_2$ pressure of 400 psi.

In contrast, the fragments formed from a hexose depend on the ketose or aldose form. Disintegration of an aldohexose leads to the fragments of a C4 aldotetrose and a C2 glycolaldehyde, while ketohexose fragmentation results in two C3 fragments, dihydroxyacetone and glyceraldehyde. With a Lewis acid catalyst, however, glucose and fructose can be inter-converted through isomerization before undergoing subsequent reactions. FIG. 27 shows that disparate yields of ML were produced from glucose and fructose, respectively, while comparable yields were seen for fructose and sucrose, the dimer of glucose and fructose (products were identified by GC/MS as shown in FIG. 39). Glucose yielded a lower amount of ML relative to fructose (37.3% versus 44.1%). The difference in the ML yields from different monosaccharides reflects the dynamic equilibrium between the isomerization, retro-aldol condensation and degradation reactions. In all cases, the conversions of both monosaccharides and disaccharides were greater than 99% after 6 hours of reaction at 240° C. and considerable yields of ML were formed using Zr-SBA-15 catalyst (FIG. 27).

Figure 40:
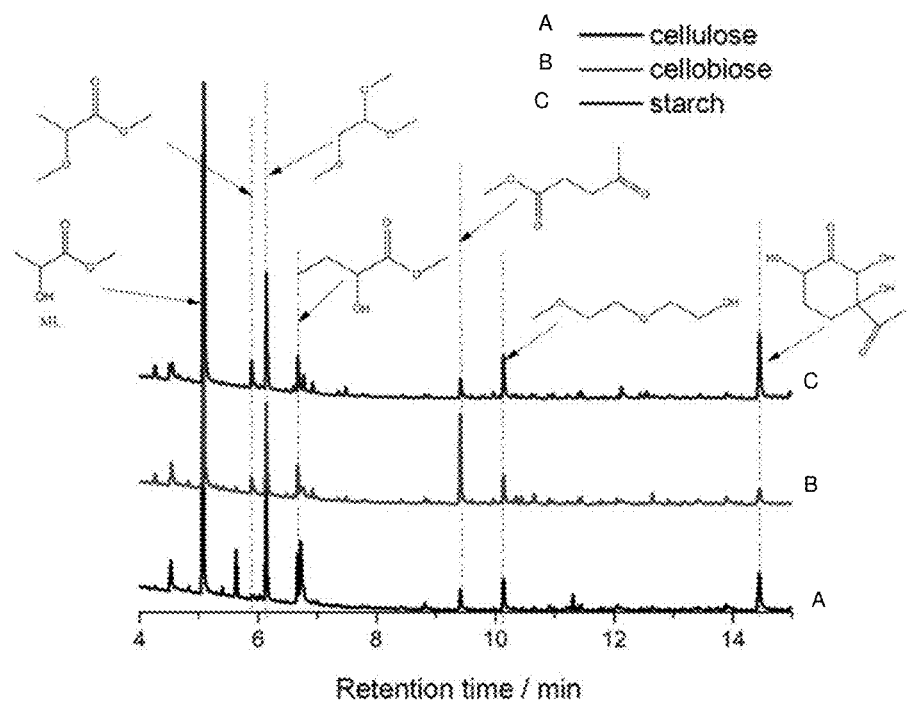
FIG. 40 is the GC/MS spectra of the products, respectively, obtained by reacting 0.2 g of cellulose, cellobiose, or starch in methanol with 0.1 g Zr-SBA-15 catalyst for 10 hours at 240° C. and an initial $N_2$ pressure of 400 psi.

Using disaccharides or polysaccharides, including cellobiose, starch and cellulose as the reactants, substantially lower conversions were observed (products were identified by GC/MS as shown in FIG. 40). Cellobiose and starch, which are soluble in methanol, reached similar yields of ML, 24.3% and 24.1%, respectively. However, only 16.7% ML was produced from cellulose at 240° C. for a 10 hours reaction, suggesting that depolymerization is the bottleneck for cellulose conversion. In order to enhance the yield of ML from cellulose, a small amount of water (5 wt %) was added into methanol to facilitate the hydrolysis of cellulose. As a result, as high as 28.1% yield of ML was obtained directly from cellulose.

Conclusion

In summary, methyl lactate was produced from various carbohydrates in methanol solutions at near critical conditions with Zr-SBA-15 catalysts. Under the reaction conditions of this Example, methyl lactate yields were 42% and 44% from pentoses and hexoses, respectively. The Zr-SBA-15 catalyst was stable to produce methyl lactate from xylose after five consecutive catalytic reaction cycles without regeneration. The Lewis acid sites on the Zr-SBA-15 catalyst facilitated the retro-aldol condensation of carbohydrates, which was the initial step for the conversion of carbohydrates to methyl lactate. Increasing zirconium loading on the SBA-15 silica framework increased the total acid strength of the Zr-SBA-15 catalyst. However, overloading of zirconium could destroy the mesoporous structure of the SBA-15 silica. The large-pore Zr-SBA-15 catalysts inhibited the yields of undesirable by-products, such as humins and furfural.

Through the probe reaction studies, it was determined that C3 aldehydes/ketones, including glyceraldehyde, dihydroxyketone, and perualdehyde, are likely intermediates in the formation of methyl lactate from a variety of carbohydrate biomass. Zr-SBA-15 also catalyzed aldol condensation of C2 aldehydes to form C4 and C6 sugars, followed by subsequent retro-aldol condensation, and finally to produce methyl lactate in high yields. The conversions of polysaccharides, such as starch and cellulose, are much more challenging than those of monosaccharides, and thus longer reaction times, as well as adding water co-solvent to facilitate the hydrolysis, was beneficial. Overall, this "one-pot" process using the Zr-SBA-15 catalyst and near critical methanol solvent is an efficient and environmentally-friendly way to produce ML from cellulosic biomass feedstocks.

EXAMPLE 3

Effect of Alkali Metal Halide on Lactate Yield

Certain embodiments of the present disclosure provide for the direct conversion of raw cellulose into alkyl lactate, a platform chemical and a commercialized "green" solvent. Conversion of cellulose in supercritical alcohols can be a tandem reaction containing three steps: (1) the hydrolysis of cellulose catalyzed by Brønsted acid sites; (2) the isomerization of glucose into fructose; and (3) retro-aldol condensation of fructose catalyzed by Lewis acid sites. The reaction can be conducted using acid catalysts, such as Zr-SBA-15 with balanced Brønsted and Lewis acidities.

The addition of alkali metal salts can improve the lactate yield of the reaction, such as by modifying the acid sites on the surface of silicate catalyst. The cation of the salt can be an alkali metal (e.g., Li, Na, K, Rb, or Cs). The anion of the salt can include a halogen (e.g., F, Cl, Br, or I). In a specific example, the alkali metal halide can be potassium chloride (KCl).

Figure 41:
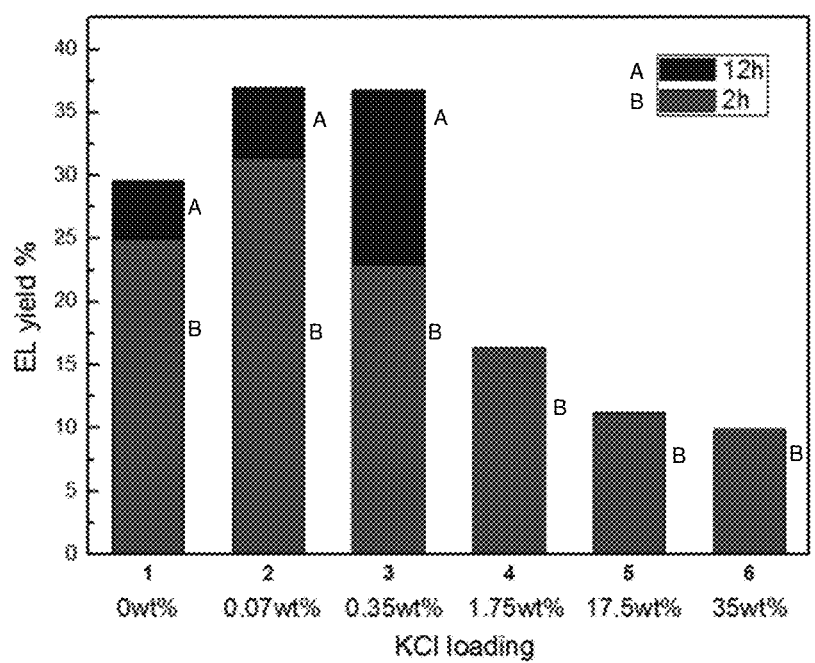
FIG. 41 is a graph illustrating the effect, after reaction for 2 hours or 12 hours, of adding KCl to the reaction mixture on the yield of ethyl lactate (EL) from cellulose, using 0.2 g cellulose, 0.1 g Zr-SBA-15 catalyst, 20 g ethanol aqueous solution (95 wt %), at 260° C. and an initial $N_2$ pressure of 400 psi.

To determine the effect of adding alkali metal halides on alkyl lactate formation, various amounts of potassium chloride were added to a mixture of cellulose, Zr-SBA-15, and 95% aqueous ethanol solution. The reactions were carried out for either 2-hours or 12-hours at 260° C. and an initial $N_2$ pressure of 400 psi. As shown in FIG. 41, after 12 hours, an ethyl lactate yield of about 37% was achieved with the addition of 0.07 wt % KCl. In contrast, without adding KCl, the yield of ethyl lactate was ~29%. The weight percentage of KCl was calculated as follows:

$$KCl \text{ wt } \% = \frac{\text{Mass of the added } KCl}{\text{Mass of the } Zr-SBA-15 \text{ catalyst}}$$

For 2-hour reactions, the yield of ethyl lactate reached about 30% by adding 0.07 wt % KCl. Further KCL loading decreased the ethyl lactate yield from about 30% to about 10%. Without intending to be limited by theory, the alkali cation could modify active Brønsted acid sites by exchanging onto an adjacent silanol group. This modification of Brønsted acid sites may result in a weaker Brønsted acidity, and thus altering the selectivity of the cellulose conversion, increasing the yield of ethyl lactate for reactions carried out at relatively high temperatures.

It is to be understood that the above discussion provides a detailed description of various embodiments. The above descriptions will enable those skilled in the art to make many departures from the particular examples described above to provide apparatuses constructed in accordance with the present disclosure. The embodiments are illustrative, and not intended to limit the scope of the present disclosure. The scope of the present disclosure is rather to be determined by the scope of the claims as issued and equivalents thereto.

We claim:
1. A method for catalytically producing organic materials from a feedstock, the method comprising:
providing a feedstock comprising a substrate comprising cellulose;
contacting the feedstock with a reaction medium comprising an alcohol and having a critical temperature and with a solid inorganic Lewis acid catalyst comprising a mesoporous material isomorphically substituted with a transition metal, the mesoporous material having a silicon-to-transition metal ratio of between about 5:1 and about 100:1;
heating a mixture comprising the feedstock, reaction medium, and catalyst to a temperature that is at least substantially the critical temperature of the reaction medium; and
maintaining the mixture at the temperature for a period of time sufficient to form ester
products from the feedstock, wherein the catalyst converts at least a portion of the cellulose into an ester of lactic acid having an ester group corresponding to the alcohol.
2. The method of claim 1, wherein the mixture is heated at a temperature of between about 220° C. and about 300° C.
3. The method of claim 1, wherein the mixture is heated at a temperature of at least about 75% of the critical temperature of the reaction medium.
4. The method of claim 1, wherein the mesoporous material isomorphically substituted with a transition metal comprises Zr-SBA-15.
5. The method of claim 1, wherein the pores of the mesoporous material isomorphically substituted with a transition metal have an average pore size of between about 6 nm and about 50 nm.
6. The method of claim 1, wherein the catalyst has an acid strength of between about 0.02 mmol/g $NH_3$ and about 10 mmol/g $NH_3$, as measured by temperature-programmed desorption of ammonia.
7. The method of claim 1, wherein the catalyst has a BET surface area of between about 600 $m^2/g$ and about 900 $m^2/g$.
8. The method of claim 1, wherein the pores of the mesoporous material isomorphically substituted with a transition metal have an average pore volume determined by the NLDFT model of between about 0.9 $cm^3/g$ and about 1.8 $cm^3/g$.
9. The method of claim 1, wherein the reaction medium comprising an alcohol and having a critical temperature is an alcohol-water mixture comprising between about 0.5% and about 10% by weight water.
10. The method of claim 1, wherein the catalyst comprises Lewis acid sites and Brønsted acid sites.
11. The method of claim 1, wherein the transition metal of the mesoporous material isomorphically substituted with a transition metal is Zr, Ti, Sn, Nb, Ga, Ge, V, or Fe.
12. The method of claim 1, further comprising:
contacting the solid inorganic Lewis acid catalyst with between about 0.001 wt % and about 1 wt % of one or more alkali metal halides before contacting the feedstock with the solid inorganic Lewis acid catalyst; or
adding between about 0.001 wt % and about 1 wt % of one or more alkali metal halides to the mixture.
13. A method for catalytically producing organic materials from a feedstock, the method comprising:
providing a feedstock comprising a substrate comprising cellulose;
contacting the feedstock with a reaction medium comprising a mixture of water and an alkyl alcohol having between 1 and 15 carbon atoms, the reaction medium having a critical temperature, and with a solid inorganic catalyst comprising Zr-SBA-15;

heating a mixture comprising the feedstock, reaction medium, and catalyst to a temperature that is at least about 75% of the critical temperature of the reaction medium; and maintaining the mixture at the temperature for a period of time sufficient to form ester products from the feedstock, wherein the catalyst converts at least a portion of the cellulose into an ester of lactic acid having an ester group corresponding to the alcohol.

14. A method for catalytically producing organic materials from a feedstock, the method comprising:

providing a feedstock comprising a substrate comprising cellulose;

contacting the feedstock with a reaction medium comprising a mixture of water and an alkyl alcohol having between 1 and 15 carbon atoms, the reaction medium having a critical temperature, and with a solid inorganic catalyst comprising a mesoporous material isomorphically substituted with a transition metal, the mesoporous material having a silicon-to-transition metal ratio of between about 5:1 and about 100:1;

heating a mixture comprising the feedstock, reaction medium, and catalyst to a temperature that is at least about 90% of the critical temperature of the reaction medium; and maintaining the mixture at the temperature for a period of time sufficient to form ester products from the feedstock, wherein the catalyst converts at least a portion of the cellulose into an ester of lactic acid having an ester group corresponding to the alcohol.

15. The method of claim 13, wherein the mixture is heated at a temperature of between about 220° C. and about 300° C.

16. The method of claim 13, wherein the mixture is heated at a temperature of at least about 90% of the critical temperature of the reaction medium.

17. The method of claim 13, wherein the solid inorganic catalyst has an acid strength of between about 0.02 mmol/g $NH_3$ and about 10 mmol/g $NH_3$, as measured by temperature-programmed desorption of ammonia.

18. The method of claim 13, further comprising:

contacting the solid inorganic catalyst with between about 0.001 wt % and about 1 wt % of one or more alkali metal halides before contacting the feedstock with the solid inorganic catalyst; or adding between about 0.001 wt % and about 1 wt % of one or more alkali metal halides to the mixture.

19. The method of claim 14, further comprising:

contacting the solid inorganic catalyst with between about 0.001 wt % and about 1 wt % of one or more alkali metal halides before contacting the feedstock with the solid inorganic catalyst; or adding between about 0.001 wt % and about 1 wt % of one or more alkali metal halides to the mixture.

20. The method of claim 13, wherein the Zr-SBA-15 has a silicon-to-zirconium ratio of between about 5:1 and about 100:1.

* * * * *